US008569050B1

(12) United States Patent
Ericsson

(10) Patent No.: US 8,569,050 B1
(45) Date of Patent: Oct. 29, 2013

(54) ENCLOSED BIOREACTOR SYSTEM AND METHODS ASSOCIATED THEREWITH

(76) Inventor: John D. Ericsson, Gulf Breeze, FL (US)

( * ) Notice: Subject to any disclaimer, the term of this patent is extended or adjusted under 35 U.S.C. 154(b) by 294 days.

(21) Appl. No.: 12/772,970

(22) Filed: May 3, 2010

Related U.S. Application Data

(60) Provisional application No. 61/175,256, filed on May 4, 2009.

(51) Int. Cl.
*C12M 1/08* (2006.01)
*C12M 1/42* (2006.01)
*C12N 1/12* (2006.01)

(52) U.S. Cl.
USPC ............ 435/292.1; 435/294.1; 435/295.2

(58) Field of Classification Search
USPC .......... 435/292.1, 294.1, 295.1, 295.2, 296.1; 422/227, 605
See application file for complete search history.

(56) References Cited

U.S. PATENT DOCUMENTS

| | | | |
|---|---|---|---|
| 1,026,578 A * | 5/1912 | Hammond ................ | 366/137 |
| 2,658,310 A | 11/1953 | Cook | |
| 2,866,297 A | 12/1958 | Marissal | |
| 3,303,608 A | 2/1967 | Hannan | |
| 3,403,471 A | 10/1968 | Clement et al. | |
| 3,439,449 A | 4/1969 | Huff | |
| 3,658,051 A | 4/1972 | MacLean | |
| 3,743,582 A | 7/1973 | Kitai et al. | |
| 3,955,318 A * | 5/1976 | Hulls ............................... | 47/1.4 |
| 3,986,297 A | 10/1976 | Ichimura et al. | |
| 4,065,386 A | 12/1977 | Rigby | |
| 4,084,346 A | 4/1978 | Stengel et al. | |
| 4,085,007 A | 4/1978 | Hawkins | |
| 4,253,271 A | 3/1981 | Raymond | |
| 4,324,068 A | 4/1982 | Anthony | |
| 4,337,315 A | 6/1982 | Fukushima et al. | |
| 4,455,374 A | 6/1984 | Schwartz | |
| 4,473,970 A | 10/1984 | Hills | |
| 4,649,117 A | 3/1987 | Familletti | |
| 4,680,314 A | 7/1987 | Nonomura | |
| 4,724,214 A | 2/1988 | Mori | |
| 4,834,872 A | 5/1989 | Overath | |
| 4,891,317 A | 1/1990 | Brown, Jr. et al. | |

(Continued)

FOREIGN PATENT DOCUMENTS

| | | |
|---|---|---|
| ES | 2 307 407 A1 | 11/2008 |
| JP | 06350119 | 12/1994 |

(Continued)

OTHER PUBLICATIONS

Wu et al. "Simulation of algae growth in a bench scale internal loop airlift reactor." Chemical Eng. Science, vol. 59 (2004), pp. 2899-2912.*

(Continued)

*Primary Examiner* — William H Beisner
(74) *Attorney, Agent, or Firm* — Allen, Dyer, Doppelt, Milbrath & Gilchrist, P.A.

(57) ABSTRACT

A bioreactor production system for growing commercial volumes of algae or other biomass in a uniquely configured, enclosed, biosecure, photo-type reactor vessel, having internal artificial growth light production as well as exterior solar energy capturing devices or the like designed to facilitate enhanced sunlight exposure for photosynthesis organism production. A unique electromagnetic field generation system is integrated with the bioreactor and its operation to substantially enhance growth rate and overall productivity.

36 Claims, 25 Drawing Sheets

(56) References Cited

U.S. PATENT DOCUMENTS

| | | | |
|---|---|---|---|
| 4,900,678 A | 2/1990 | Mori | |
| 4,952,511 A | 8/1990 | Radmer | |
| 4,970,166 A | 11/1990 | Mori | |
| 5,001,066 A | 3/1991 | Hitzman | |
| 5,024,759 A | 6/1991 | McGrath et al. | |
| 5,030,196 A | 7/1991 | Inoue | |
| 5,121,708 A | 6/1992 | Nuttle | |
| 5,137,828 A * | 8/1992 | Robinson et al. | 435/292.1 |
| 5,614,378 A | 3/1997 | Yang et al. | |
| 5,670,046 A | 9/1997 | Kimmel | |
| 5,776,349 A | 7/1998 | Guelcher et al. | |
| 5,846,816 A | 12/1998 | Forth | |
| 5,910,254 A | 6/1999 | Guelcher et al. | |
| 5,951,875 A | 9/1999 | Kanel et al. | |
| 5,958,761 A | 9/1999 | Yogev et al. | |
| 5,961,831 A | 10/1999 | Lee et al. | |
| 6,000,551 A | 12/1999 | Kanel et al. | |
| 6,083,740 A | 7/2000 | Kodo et al. | |
| 6,370,815 B1 | 4/2002 | Skill et al. | |
| 6,479,277 B2 | 11/2002 | Duncan | |
| 6,509,188 B1 | 1/2003 | Trosch et al. | |
| 6,524,486 B2 | 2/2003 | Borodyanski et al. | |
| 6,579,714 B1 | 6/2003 | Hirabayashi et al. | |
| 6,602,703 B2 | 8/2003 | Dutil | |
| 6,615,767 B1 | 9/2003 | Untermeyer et al. | |
| 6,667,171 B2 | 12/2003 | Bayless et al. | |
| 6,675,047 B1 | 1/2004 | Konoplev et al. | |
| 6,986,323 B2 | 1/2006 | Ayers | |
| 7,135,332 B2 | 11/2006 | Ouellette | |
| 7,172,691 B2 | 2/2007 | Dunlop et al. | |
| 7,425,441 B2 | 9/2008 | Broneske et al. | |
| 7,473,008 B2 | 1/2009 | Crabb et al. | |
| 7,682,821 B2 | 3/2010 | Woods et al. | |
| 7,748,891 B2 * | 7/2010 | Tysse et al. | 366/174.1 |
| 2005/0239182 A1 | 10/2005 | Berzin | |
| 2005/0260553 A1 | 11/2005 | Berzin | |
| 2006/0035370 A1 | 2/2006 | Lee et al. | |
| 2007/0082328 A1 | 4/2007 | Rudd | |
| 2007/0092962 A1 | 4/2007 | Sheppard | |
| 2008/0009055 A1 | 1/2008 | Lewnard | |
| 2008/0086939 A1 | 4/2008 | Dunlop et al. | |
| 2008/0153080 A1 | 6/2008 | Woods et al. | |
| 2008/0178739 A1 | 7/2008 | Lewnard et al. | |
| 2008/0220515 A1 | 9/2008 | McCall | |
| 2009/0011492 A1 | 1/2009 | Berzin | |
| 2009/0029445 A1 | 1/2009 | Eckelberry et al. | |
| 2009/0035835 A1 | 2/2009 | Slavin | |
| 2009/0130706 A1 | 5/2009 | Berzin et al. | |
| 2009/0137031 A1 | 5/2009 | Hirabayashi | |

FOREIGN PATENT DOCUMENTS

| | | |
|---|---|---|
| WO | WO 2005/059087 A1 | 6/2005 |
| WO | WO 2007/044386 A2 | 4/2007 |
| WO | WO 2008/051865 A2 | 5/2008 |
| WO | WO 2008/055190 A3 | 5/2008 |
| WO | WO 2008/074906 A1 | 6/2008 |
| WO | WO 2008/134010 A2 | 11/2008 |

OTHER PUBLICATIONS

Li et al, Effects of Magnetic-Field on the Nutrition of Spirulina Platensis and Mechanisms Analysis, ACTA Biophisica Sinca vol. 17 No. 3 Sep. 2001 p. 591.

Li et al, Effects of Electromagnetic Field on the Batch Cultivation.., Bioresource Technology 2007 700-705 vol. 98, No. 3 (Abstract only).

Pietruszewski et al; Electromagnetic Fields and Electromagnetic Radiation as non-invasive.., International Agrophysics 2007, 95-100, 21.

The Energy Blog Jun. 17, 2005 Biodiesel from Algae is Here! p. 1-2 http://thefraserdomain.typpad.com/enegy/2005/06/University of n.html.

Shupak et al; Theraputic uses of Pulsed Magnetic-Field Exposure: a Review; Radio Science Bulletin Dec. 2003, pp. 9-32 No. 307 U.R.S.I.

Kositski et al; Inyluence of High-frequency Electromagnetic Radiation at Non-Thermal Intensities..; No Place to Hide, Newsletr of Cellular Phone Taskforce, vol. 3, #1, Feb. 2001.

\* cited by examiner

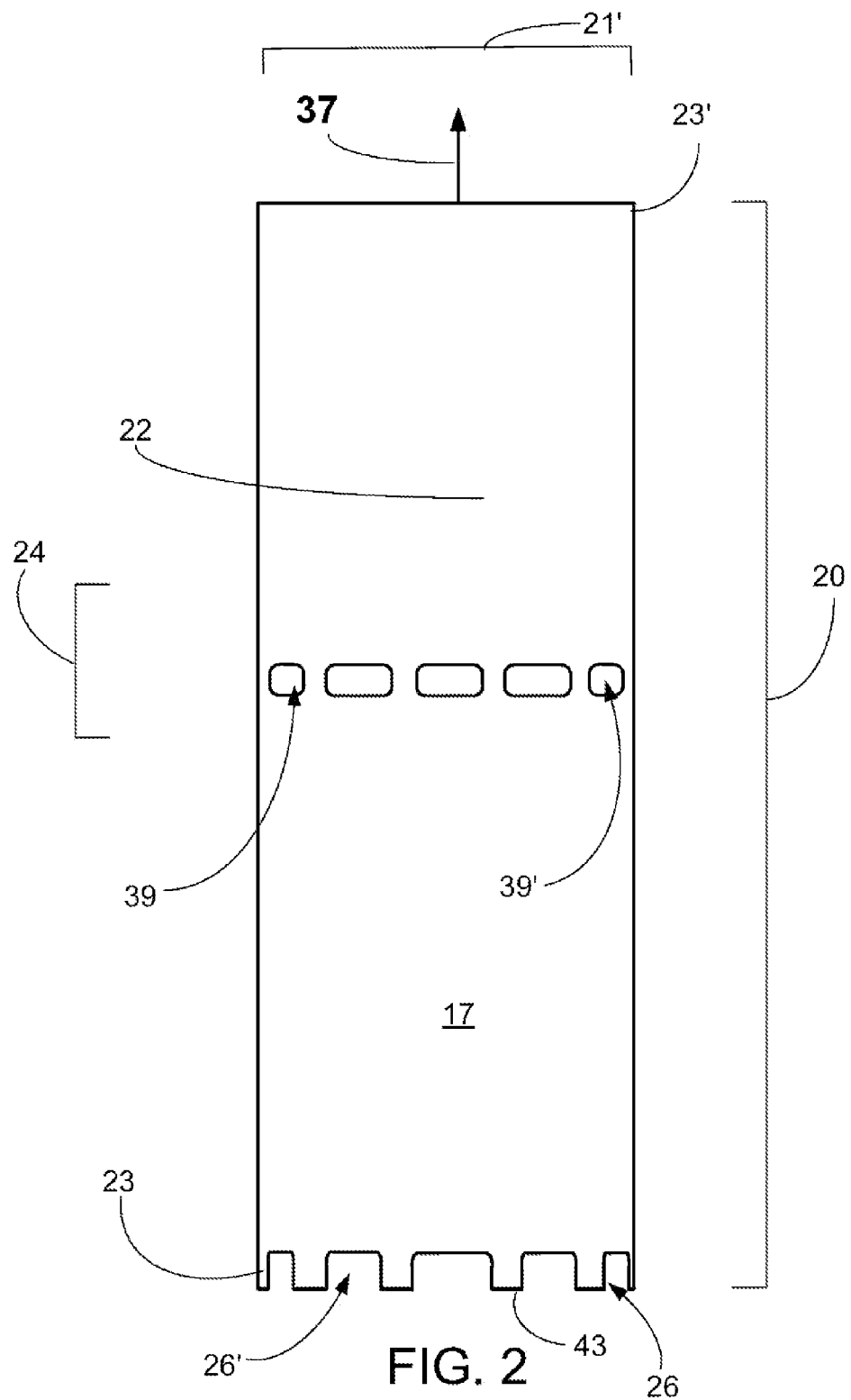

(45° Angle) 118'

(30° Angle) 118

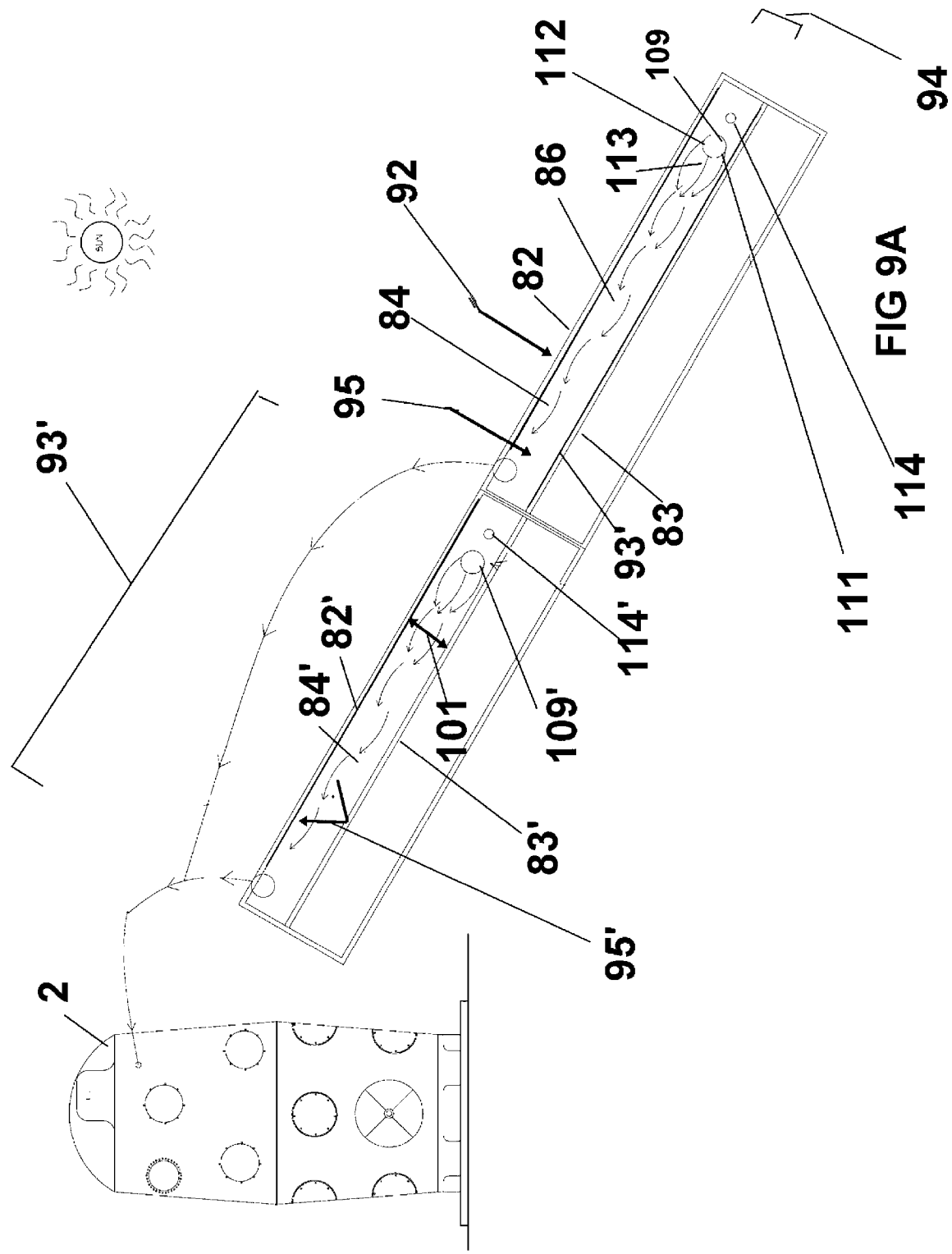

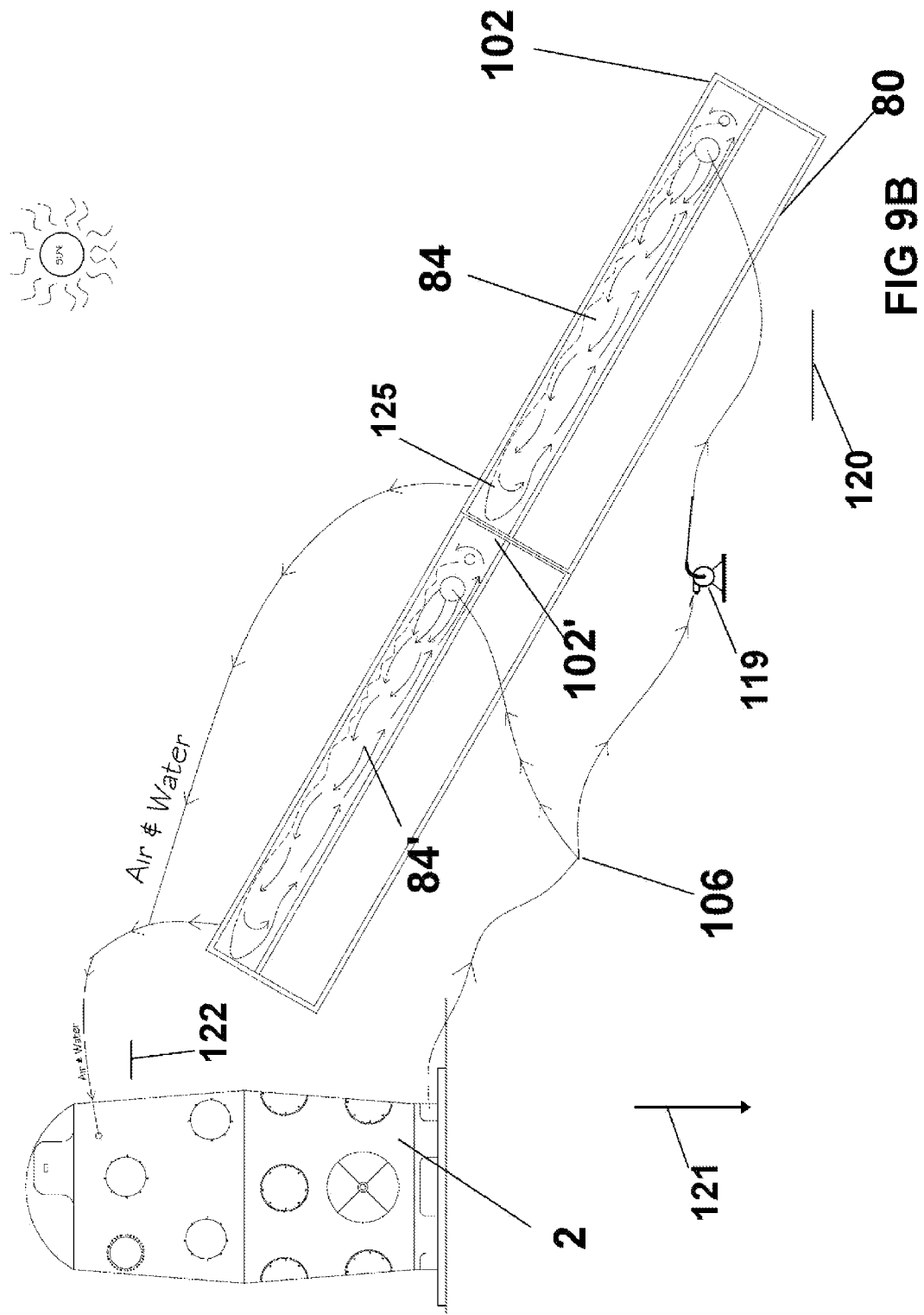

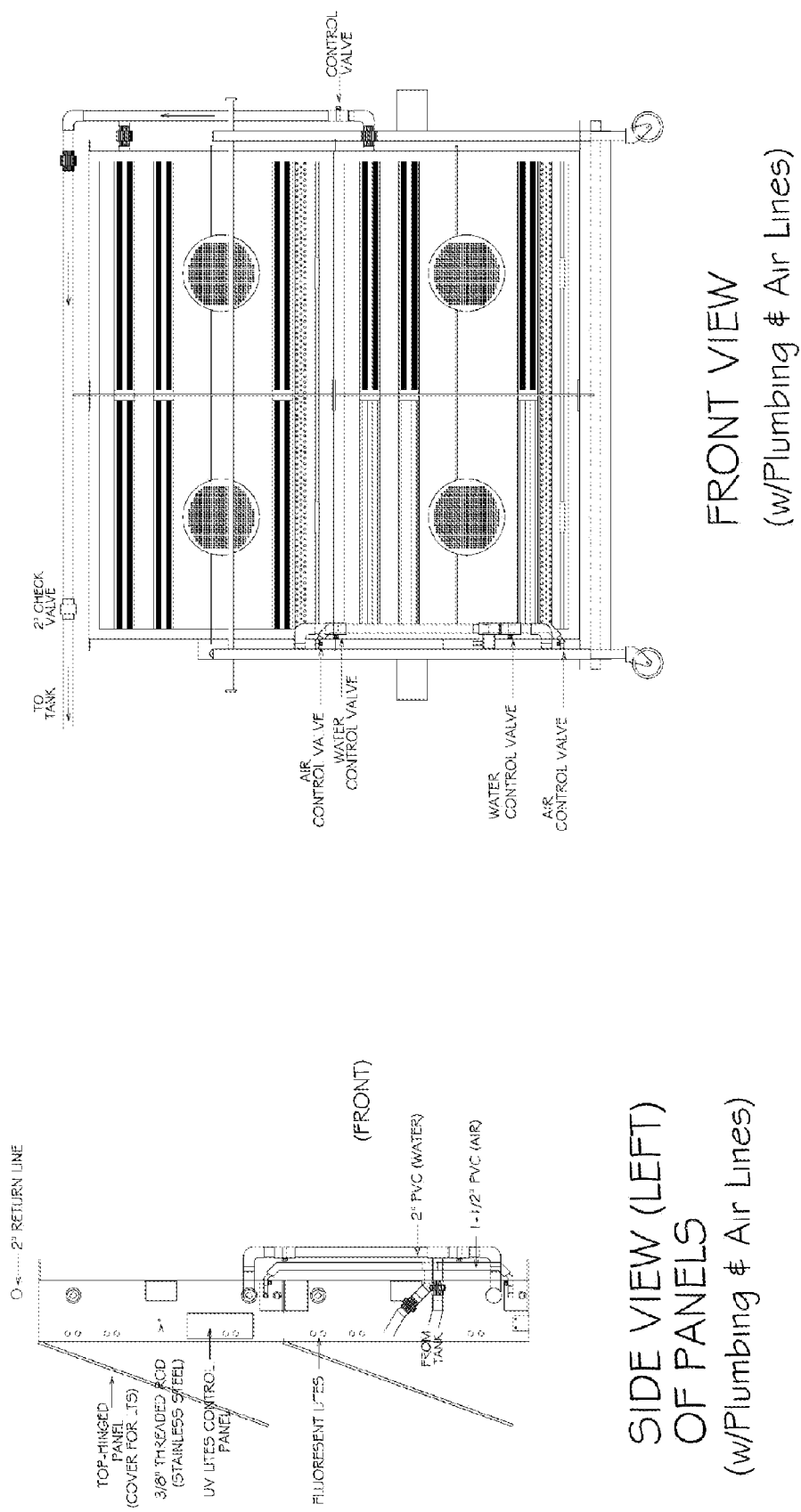

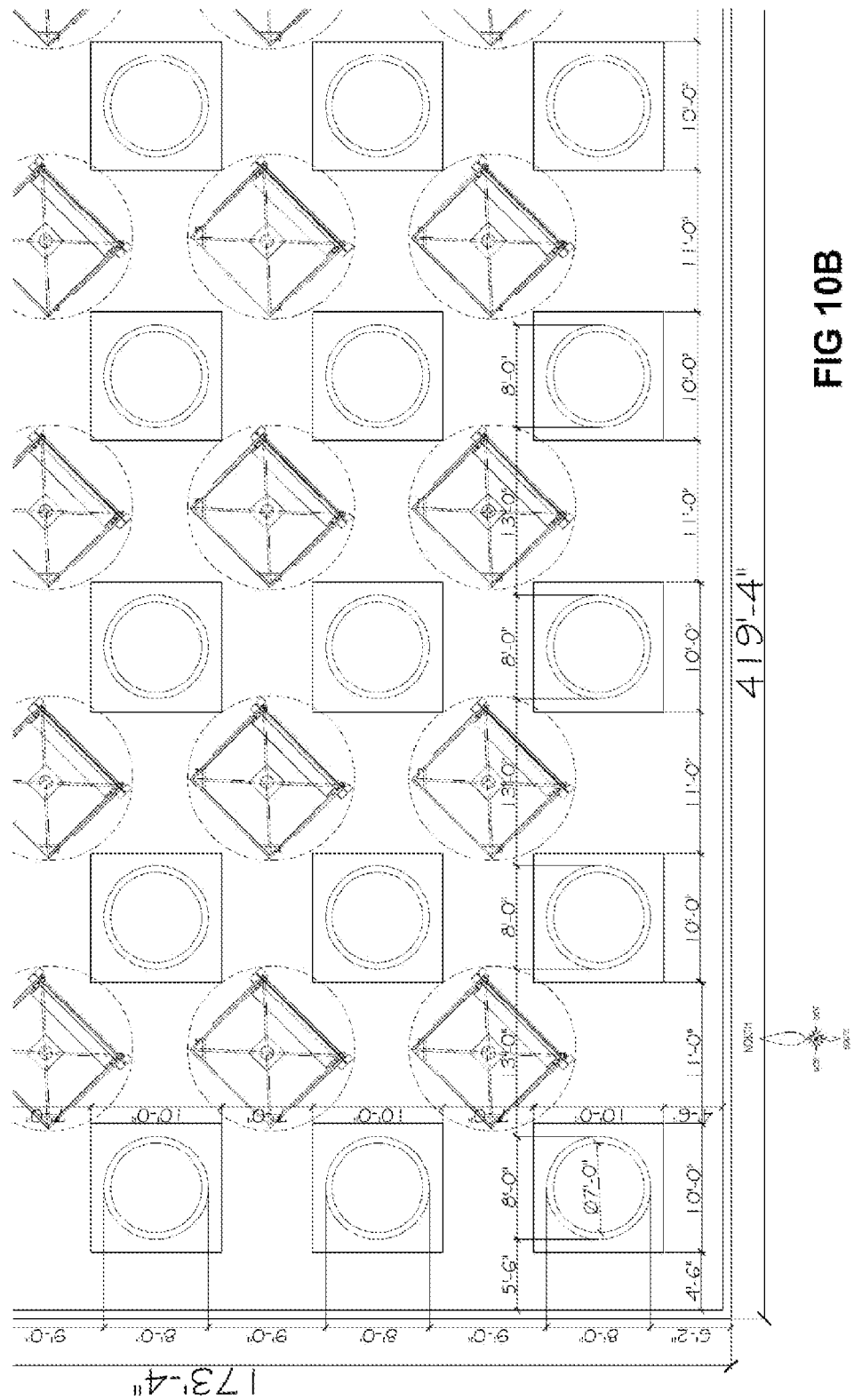

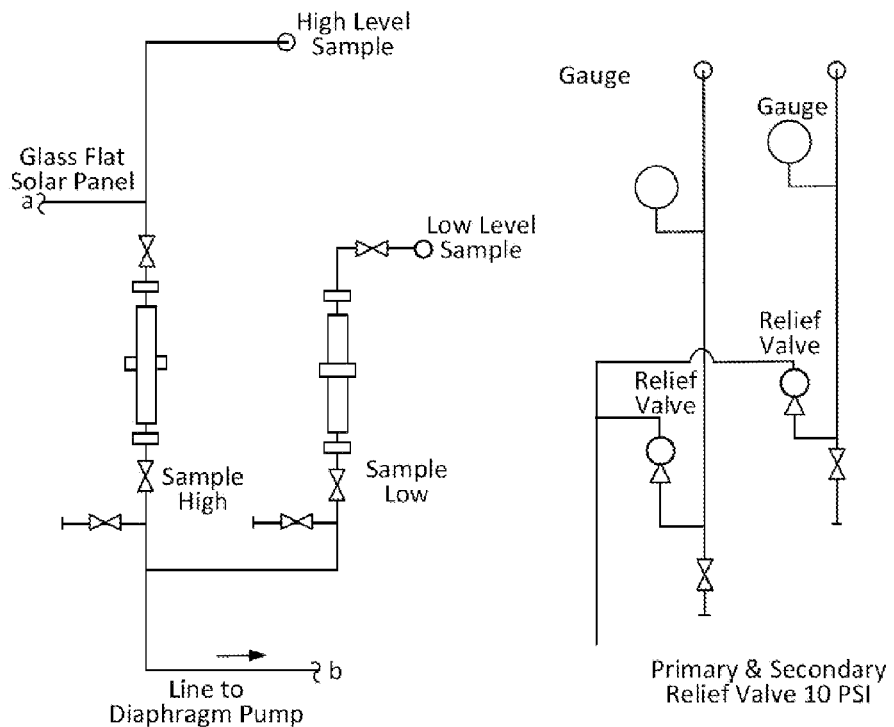
FIG. 11A
Detail A
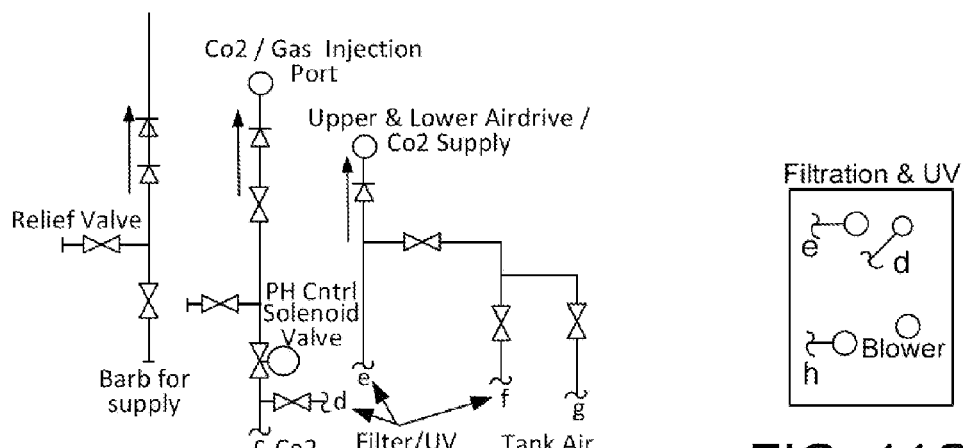
FIG. 11B
Detail B
FIG. 11C
Detail C

ENCLOSED BIOREACTOR SYSTEM AND METHODS ASSOCIATED THEREWITH

CROSS REFERENCE TO RELATED APPLICATIONS

The present application claims the benefit of Provisional Patent Application Ser. No. 61/175,256, filed May 4, 2009 entitled ENCLOSED BIOREACTOR SYSTEM AND METHODS ASSOCIATED THEREWITH, the contents of which are hereby incorporated herein by reference thereto.

FIELD OF THE INVENTION

The present invention relates to two interrelated, enclosed bioreactor systems, and in particular to a production system for growing commercial volumes of algae or other biomass in two uniquely configured enclosed, biosecure, photoreaction-type bioreactor vessels. The bioreactor system of the present invention provides internal artificial grow light production, as well as exterior solar energy capturing features, for facilitating enhanced sunlight exposure for photosynthesis organism production. In addition, two unique electromagnetic field generation systems are associated within the core biomass reactor to substantially enhance growth rate and overall productivity.

The present system may be utilized to grow feed grade biomass, ethanol fuel or biodiesel, as well as nutrients, pharmaceuticals, and other valuable compositions via the cultivation of algae or the like. Also, the system can utilize tons of flue gas Co2 pollution emissions from fossil fueled plants in a carbon sequestration capacity as well, so as to enhance algal productivity which consumes hazardous environmental gases.

GENERAL BACKGROUND DISCUSSION OF THE INVENTION

Algae has been recognized as a valuable resource, with proper cultivation and processing providing many products including fuels, feed, and a diverse array of chemicals which have uses in pharmaceuticals, and nutritional products like Omega 3 oils, which can be valued at over $500 per gallon.

The production of algae has sustainability advantages when compared to traditional land based crops and fossil fuels. Significant carbon savings are achieved by using energy-rich algae as a feedstock and source of biofuel, since algae consumes more harmful Co2 gas than is generated when its products are used as fuel or within other chemical products. Based on a carbon cost of $15 per ton (the projected carbon cost in 2012 under the post-Kyoto Treaty, the algal advantage has been estimated at a sustainable $0.20 per gallon with carbon costs expected to rise until at least 2050 because of increasingly high-carbon reduction targets.

Algae has the potential to provide a cost effective, economically sustainable substitution for existing fuels and feeds, which have been traditionally produced from fresh water intensive, agriculture land-based crops such as corn and soybeans, and from fossil petroleum. The controversy regarding the use of corn and other food to produce biofuel is well known, with the U.S. liquid transportation fuels market estimated at approximately 180 billion gallons per year and the global fuels market approaching 600 billion gallons per year.

Algal biomass is known to provide a high-protein concentrate (or higher-purity isolate) suitable for animal use or fish feed, and can be made suitable for human consumption. In fact, the ancient Mayan civilization made a bread type food out of Spirulina (Arthrospira sp.) blue-green algae grown and gathered from within their freshwater lakes. Today there is an established market for these algae type protein supplements; in the U.S. alone, the protein ingredient market was 2.40 billion pounds, valued at $3.9552 billion in 2007.

At the time of this writing, soybeans sell for approximately $0.12 per pound, whereas soy protein isolate sells for approximately $1.92 per pound. The nutritional value of several alga species show their protein content to be up to five times easier to digest as human protein than meat or soybean meal. (Biological value measures the degree to which the body can absorb and use the protein, with a higher number suggesting greater absorption and utilization.)

Biofuels Digest has projected that global algal fuel production will reach 1 billion gallons by 2014; other sources suggest that production volumes will not reach these levels until later in the decade.

Either way, algae derived transportation fuels may constitute only 0.0001% or one/one thousandth of the 2014 world fuel needs without giving demand values for other valuable algae products.

It is well known that algae may contain over 50% oil by weight, depending upon the species; other species can contain cellulose or sugar, either of which can be synthesized into fuels, in the amount of up to 40% by weight, and after processing, the remaining 60% to 70% of biomass can be used for valuable non-fuel applications, including:

Specialty Chemicals;
Nutraceuticals and Pharmaceuticals;
Feeds as well as food;
Naturally derived Pigments;
Products for Personal Care; and
Other unique products This indicates that it is likely that first-mover algae companies that have commercialized algae production systems operational in the 2010s, will enjoy an pronominal opportunity to enter the bio-oil, chemicals and feeds market without triggering an oversupply market condition for possibly decades.

There have been many attempts to provide a cost effective, enclosed bioreactor system for the cultivation of algae on a commercial scale for biofuel, biomass, and byproduct production, however, none are believed to provide a system which does so in an economically viable and sustainable manner.

Accordingly, there exists a long felt, but unresolved need to provide a fabrication-cost effective, enclosed and controlled bioreactor system for large scale commercial production of protein and energy-rich algae or other forms of biological biomass grown by photosynthesis or the like which is efficient in operation, while operating on an economically viable and sustainable basis.

GENERAL SUMMARY DISCUSSION OF THE INVENTION

The present invention relates to two bioreactor units creating a system, and in particular to an algae fuel/protein production system, capable of growing commercial volumes of energy-rich algae biomass in enclosed, biosecure, photo-type bioreactor vessels. Artificial and natural sunlight may be utilized in the present invention for continuous 24 hour a day operations. Further, an auxiliary solar energy capturing unit with translucent panels is provided to circulate the entire biomass inside of the core 4000 gallon bioreactor rapidly through an exterior flat panel reactor, to expose all the microorganism in the entire system to either natural sunlight in the day time or with electric grow lights for night time stimulation. The present 4000 gallon capacity system is designed to produce one ton of concentrated algae or other cellular organism biomass per 24-48 hr period.

The present enclosed system is designed to digest CO2 type emission greenhouse gases commonly produced in hydrocarbon fueled electric generation plants, and transform these environmentally harmful waste byproducts into a significant resource, for CO2 neutral production of biofuels, chemicals and proteins from cellular organisms. In addition, the protein and cellulose by-products can be utilized in a variety of products such as feedstock for animals, as well as human food nutrients, while the algae lipid oils can be processed to produce valuable Omega-3 fatty acids, pharmaceuticals, cosmetics, chemicals and/or biofuels.

The preferred embodiment of the present invention provides a cost efficient, assembly line-type production system for establishing large scale production plants for growing millions of gallons of energy-rich algal biomass with high oil and protein content. The design utilizes high energy efficiency artificial grow light devices (shown as light emitting diodes or LEDs which are rectifying semiconductor devices which convert electrical energy into electromagnetic radiation). The wavelength of the adjustable, high lumen, grow-light devices consist of specifically chosen LED's which covers the entire spectrum of photosynthesis light energy range from 400 nanometers (nm) to 465 nm in blue light mixed with 620 to 750 nm in red light.

These special LED grow-light units provide a high intensity grow-light ideally suited for algae photosynthesis, while consuming relatively less electricity, when compared to traditional grow-light systems. While LED's and florescent grow lights are disclosed in the preferred embodiment, this is not intended to be limiting, and other light sources could function in their capacity.

As discussed, an auxiliary flat panel glass bioreactor system is utilized with the core bioreactor to increase the exposure time of the entire biomass within the system to photosynthesis energy. The core bioreactor utilizes other forms of electromagnetic and millimeter wave energy producing units within the system for 1). increasing cell division (mitoses) and 2). for separation of the lipid oil from within the algae cell while utilization either saline (seawater) or freshwater, depending upon the algal species being raised.

The core bioreactor containment vessel of the exemplary embodiment is made primarily of fiberglass (although other materials can be utilized), the vessel having high clarity acrylic dome lenses which employ energy efficient, focused LED grow lamps to project visible radiation of the desired photosynthesis wavelength spectrum through the acrylic dome lenses into the vessel during non-daylight hours, to maintain optimal biomass production on a continuous basis. Marine algae, which may contain from less than 40% to over 60% lipids, or other microalgae/yeast and/or energy producing bacteria, including genetically enhanced varieties, may be cultured in the present biosecure system.

The liquids from the harvested biomass may be dewatered and converted into "green" biofuels. For harvesting, the preferred embodiment of the present invention utilizes a Total Fluid Management (TFM) program which utilizes a unique dewatering membrane filtration system produced by the Pall Corporation which will cost effectively separate the mature algae cells from the biomass liquid into a 30% or less moisture content "algae paste" and return the filtered liquid biomass back to the bioreactor system. Next, the first proposed harvesting method uses the SCF Technologies CATLIQ™ brand biomass conversion process, which is designed to transform the molecular elements of the water/hydrogen molecules with the cellulose, protein and lipid oil content within the algal cells into bio-crude oil on a 2.5 to 1 transformation basis. Several other new filtration and fuel processes and/or existing techniques and equipment may alternatively be used in the biomass transformation process, including the Fischer-Tropsch Synthesis process as well as other existing biodiesel refining systems presently used for agricultural biomass/seed oil processes.

The present system fulfills a long-felt but unresolved need to provide a cost effective assembly-plant type apparatus and method of producing commercial volumes of algal biomass. At present, there does not exist a reliable, sustainable and economic algal-biomass production systems due to the cost of production when compared to other forms of energy biomass like corn and soy bean oil based upon land-based agricultural products for biofuels.

The present system seeks to lower the total production costs for protein and energy-rich algal biomass, making same competitive with other biomass and seed oils utilized for fuel production, as well as competitive in cost with fossil fuels and the like, while providing consistency of production in an enclosed, reliable, high efficiency process.

The present system's use of two enclosed bioreactor systems (the core bioreactor and auxiliary flat panel bioreactor) optimizes the use of artificial and/or natural sunlight. The present system is further enhanced with the selective utilization of a finely tuned electromagnetic energy field associated with the upper flow tube and/or dome area of the core bioreactor, which in the exemplary embodiment of the invention has about 4000 gallon capacity, the exemplary embodiment configured with the capacity to produce about one ton (moist weight) of concentrated algae or other cellular organism biomass per 24- to 48-hour period.

The core bioreactor containment vessel of the exemplary embodiment of the present invention has a completely sealed and pressurizable growing environment to prevent contamination of the cell culturing process, has thermally insulated outer walls, and is thermostatically-controlled with built-in heat and/or cooling exchangers to maintain optimal propagation temperature therein for maximum biomass-growth potential which is ideally suited for genetically altered or "engineered" cellular organisms that cannot be grown in open ponds or raceways.

In addition to providing maximum cell division rates via optimal energy conditions, the system utilizes an innovative electromagnetic stimulation technique wherein selective electromagnetic millimeter wave exposure is provided within the vessel at a frequency and strength so as to promote maximum algal cell reproduction rates.

It has been well established by numerous new publications and medical breakthroughs that pulsed electromagnetic fields (PEMF) have made significant contributions to the improvement of basic cellular functions including reproductive capacity, as well as other functions.

In the preferred embodiment of the present invention, a tunable millimeter wave generator with a concomitant wave guide transponder/antenna associated with the top of the reactor dome is positioned to provide within the reactor a controlled electromagnetic millimeter wave field formed to generate the stimulation of algae cell division (mitosis) by enhancing the regeneration cycle of the algae.

The millimeter wave device may be in the vicinity of the clear or otherwise millimeter wave shielded acrylic dome associated with the top of the core bioreactor, and is configured to emit a special frequency millimeter EMF wave with exposure times that may vary from 20 minutes per day to 24 hours per day, dependant upon the FLOWCAM observed cell-division rate.

The cell division rate in the present embodiment is monitored by a continuous digital cell-counting device, the FLOWCAM imaging system manufactured by Fluid Imaging Technologies of Maine (www.fluidimaging.com), the explanation of which is incorporated herein by reference.

The FLOWCAM system combines the capabilities of flow cytometry and microscopy and automatically counts, images, and analyzes the cells in a discrete sample or a continuous flow. As a result, the FLOWCAM provides data collection instantly thus generating cellular health observations and growth rates up to 500 million cells per ml of fluid and therefore creates an effective means of monitoring and managing not only the cultivation and well being of the living biomass, but also to monitor and control the various stimuli being used to maximize biomass production.

The combination of these technologies within this unique bioreactor design gives an immediate cause and effect understanding of the cause and effects upon single or multiple cell water born organisms as they are exposed to a designed electromagnetic field, artificial or natural sunlight and nutritional or other stimuli.

In addition, a computerized electronic monitoring system is also incorporated within the invention that will continuously track the amounts of natural and artificial solar energy emitted into the bioreactor as well as control and maintain the bio-water chemical and environmental conditions, e.g., vessel pressure, Ph, ORP, O2, CO2, temperature, salinity, nitrogen, nitrate, chlorine, potassium and many other parameters within the cell propagation chamber.

The air lift circulation system which mixes and delivers C02 gas and ambient air into the main and glass panel bioreactors is designed to filter all air borne particles down to 10 microns and sterilize the air flow with high intensity electric UV lamps, to prevent potential contamination of the biomass with any bacteria, virus or other competitive organism coming into the air lift system from entering the organism propagation chambers within the bioreactors.

In addition, a Helmholtz electromagnetic coil device, a sophisticated electromagnetic field generator system, may be attached to the upper flow tube (also referenced as the "control tube") or elsewhere within the bioreactor, so as to create a controllable electromagnetic field tuned so as to generate therapeutic stimulation of algae cell production (mitosis).

It is noted that, although the Helmholtz electromagnetic coil device is mentioned, other electromagnetic coil devices may likewise be suitable, and thus the reference to the Helmholtz device is not intended to be limiting.

A Helmholtz coil is a parallel pair of identical circular wire coils spaced one radius apart and wound so that the current flows through both coils in the same direction.

This winding results in a very uniform magnetic field between the coils with the primary component parallel to the axes of the two coils. The uniform field is the result of the addition of the two field components which are situated parallel to the axes of the two coils, and the difference between the components to the axes.

In the exemplary embodiment of the present invention, the electromagnetic coil device in the form of a Helmholtz coil will be installed about the center four foot diameter flow tube within the reactor vessel, about two feet from the top of the tube, with about 24.5 inches of separation between the coils.

The lower light ranges of solar energy (light and electromagnetic energy waves) can be simulated in part by this device and thereby improve cellular heath and increase rates of reproduction.

The Helmholtz coil device is expected to generate an electromagnetic field within the bioreactor at a strength of between 15 and 100 Hz at 2 ut, 4 ut, 6 ut, 8 ut up to 100 ut for improved cellular growth rate and higher frequencies for cell rupture.

As the second proposed harvesting process, electromagnetic energy is used to separate the biomass into the component lipids and polysaccharide (cellulose) fractions. In this operation, an infusion of CO2 gas is injected into the liquid medium within the flow tube of the bioreactor containment vessel (although it could be done elsewhere in the system) in order to effect a drop in the pH (acidic condition) in the liquid medium. This action weakens the algal cell body. Either the millimeter wave or the Helmholtz EMF source generator, may be tuned to provide a pulsed energy field at a precise frequency and field strength which can create the impetus to fracture the organism cell wall.

In this case, cell density is monitored, the appropriate electromagnetic energy frequency for optimal cell rupture is selected, and the cell contents (lipids and polysaccharide/protein components) are irradiated with EMF energy, split and separated in an affiliated system settling tank thereby enabling gravity separation of the lipids from the cell detritus after fracturing.

It is estimated that 100 of the bioreactors described in the present invention, arranged and operating in serial production mode, have the potential to produce some 100 or more barrels of algae bio-crude per day, in addition to 10 metric tons of a concentrated algae biomass, useful for pharmaceutical, human or animal nutrition applications.

The present system may be sited on land with minimum green house weather protection, and is suitable for siting offshore as, e.g., abandoned oilfield production platforms. A large number of 4000 or larger gallon reactor units can be placed within a building with a corresponding number of the glass solar panels reactor on the roof (like photovoltaic panels) for concentrating solar energy circulated below into the core algae biomass bioreactor system inside in a temperature controlled manner. Many other applications and locations are suitable in both cold and warm weather climate.

As discussed, the present system utilizes a novel, innovative auxiliary flat panel glass bioreactor for increasing sunlight exposure (alternatively referenced as a "bio-panel"), which is intended to be situated outside the core reactor vessel and positioned so that the glass plates face the arc of the sun as it tracks across the sky. Such an arrangement would, naturally, be positioned so that it is directly exposed to the sun and maintained via a motorized sun tracking device.

The "bio-panel" is provided to further accelerate photosynthesis by means of increasing the amount of photon exposure to the growth medium by flowing the liquid biomass through a thin glass cell with 64 square feet of surface area. The Ph adjusted water borne biomass will gravity flow from the bottom of the core 4000 gallon core reactor tank to the bottom of the 4 inch wide glass bio-panel (the exemplary embodiment measuring 8 feet by 8 feet) where it is further pumped to the top of the bio-panel and returned to the top of the core reactor for biomass reincorporation and for further EMF stimulation.

The 64 square foot area of the bio-panel also has an array of up to 36 artificial solar lights consisting of both 40 watt florescent grow lights and 90 to 240 watt LED grow lights attached to the back side of the bio-panel which are activated by a light sensor that turns the selected artificial grow lights on and off with sunrise and sunset or manually for poor solar radiance days. The importance of the bio-panel is to facilitate maximizing the exposure of the entire 4000 gallons of microorganism biomass to natural solar, artificial solar and EMF energy every 2 hours, during day and night conditions, so as to increase the growth rate of the biomass under production. All these features will be further explained and described herein.

Calculations based on earlier studies by Hirata et al. and Ohtaguchi et al. indicated that a little more than 1,000,000 m.sup.2 bioreactor surface area is required to reduce the CO2 emission of a typical 500 MW coal-fired generation unit by 25%. This translates into 257 acres of water surface area for a high-density pond raceway type reactors. Using the present Ericsson design of incorporating the novel roof-top or ground based solar collection panel and commercial volume photobioreactor technology described herein, the required area decreases to 100,000 square feet within a building or 200,000 square feet in a greenhouse protective enclosure.

An enclosed reactor system of this size is far less formidable to site and construct, and is certainly manageable compared to siting and operating a 257-acre pond near a power plant, which would create numerous groundwater contamination concerns. In addition, pond type biomass systems have a high risk of biomass loss due to changing temperature and weather conditions and contamination by unwanted water/air borne organisms that eat or compete with the algae biomass under pond types of biomass production.

Further, an enclosed reactor has a number of options for delivery of the CO2, including as raw flue gas. Bubbling flue gas through a 257 acre pond would be illegal, as the ground level contamination would be pose extreme health threats to the area. Therefore, a pond type raceway biomass reactor would require CO2 separation before utilization, eliminating virtually any energy advantage of a pond type bioreactor in CO2 control.

Non-photosynthetic carbon sequestration is a significant net energy loss. Separation of CO2 from the flue gas either requires refrigeration or mechanical action. The sequestration (compression or pumping) of the separated CO2 also requires significant energy. All totaled, CO2 sequestration by non-photosynthetic means will require 25-40% of the power generated by a host utility compared to 2-5% for the hybrid solar photobioreactor.

That means more fossil fuel will have to be burned to produce the same net power output before sequestration. This also has direct implications on the environment. Because more fuel must be burned to power the sequestration systems, more associated pollutants will be released. Only a system utilizing solar electromagnetic energy to produce biomass, as described in this invention, will require minimal power generation to minimize CO2 emissions.

The improved illumination and electromagnetic energy design as configured in the combined photobioreactors a) takes advantage of focused, low energy/high intensity LED grow lights, b) dramatically increases the surface area exposure rate of liquid biomass to photosynthesis energy c) substantially increases the rate of mitoses (cell division) in photosynthetic organisms, d) demonstrates the ability to achieve much higher volumetric carbon fixation rates, e) filters unwanted UV and IR radiation from the bioreactor, f) and increases the amounts of electromagnetic energy stimulation and sunlight utilization cost-effectively when compared to earlier photobioreactors.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 2 is a side view of the bioreactor flow tube of the present invention, illustrating the medial flow apertures and the lower flow cutouts.

FIG. 4 is a top, cross-sectional view of the bioreactor flow tube of FIG. 2 illustrating centrally-spaced and longitudinally-placed first and second radiator baffles formed to allow the temperature of the vessel contents to be adjusted, concomitantly forming a central conduit there through.

FIG. 9A is second, side, partially cut-away view of the flat panel bioreactor of FIG. 9, illustrating circulation of liquid and suspended biomass therethrough.

FIG. 9B is a third, side, partially cut-away view of the flat panel bioreactor of FIG. 9, illustrating the circulation of air bubbles, liquid and suspended biomass therethrough.

FIG. 9C is a side, partial view of the left side of the flat panel bioreactor.

FIG. 9E is a frontal view of the flat panel bioreactor of the present invention.

FIG. 10B is a top view of the bioreactors and partial facility structure of FIG. 10A.

FIG. 11A is a flow diagram providing detail on reference letter "A" in FIG. 11.

FIG. 11B is a flow diagram providing detail on reference letter "B" in FIG. 11.

FIG. 11C is a flow diagram providing detail on reference letter "C" in FIG. 11.

DETAILED DESCRIPTION OF THE INVENTION

Figure 1:
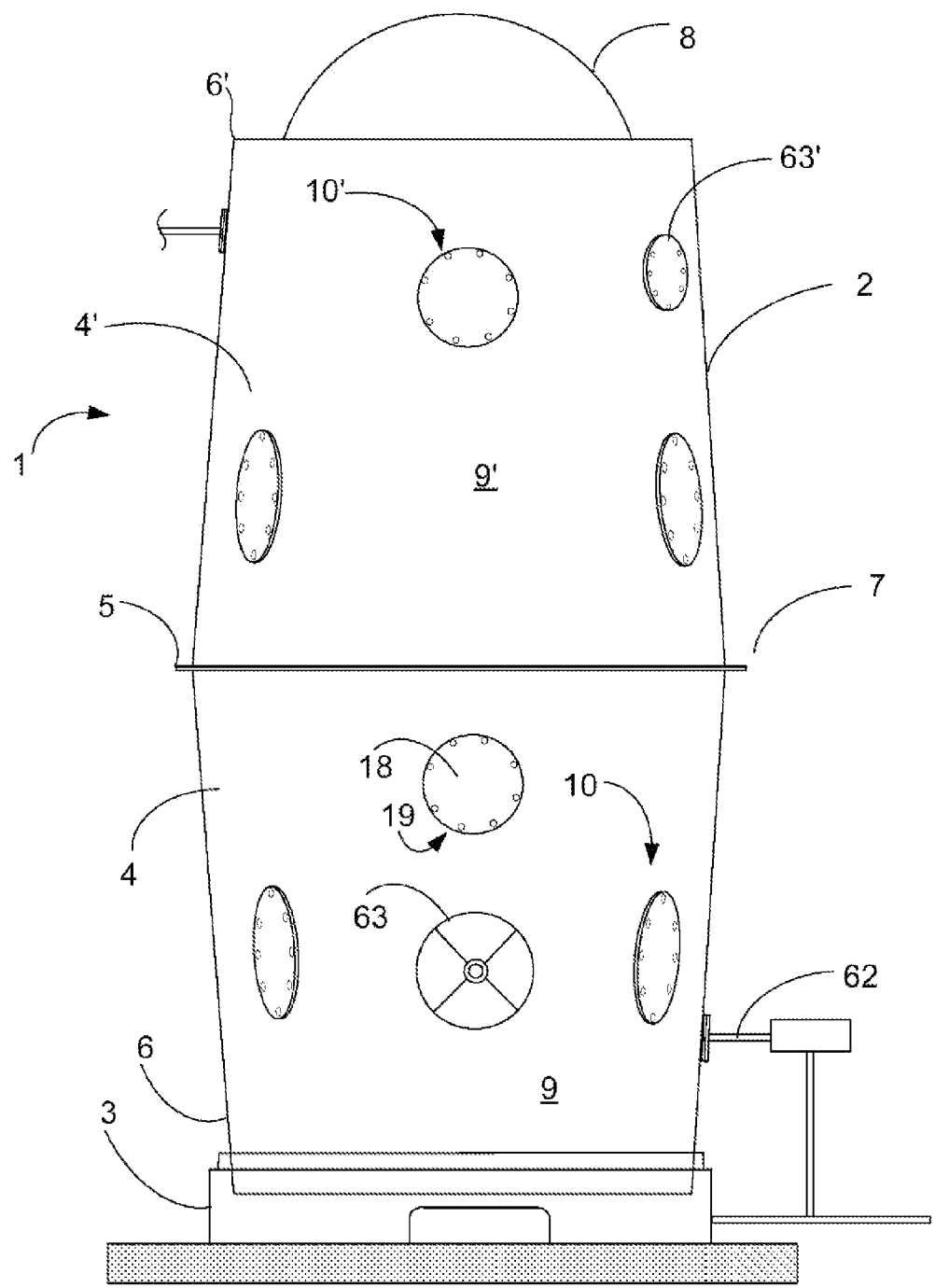
FIG. 1 is a side, exterior view of the bioreactor vessel/body/tank of the preferred embodiment of the present invention.
Figure 1C:
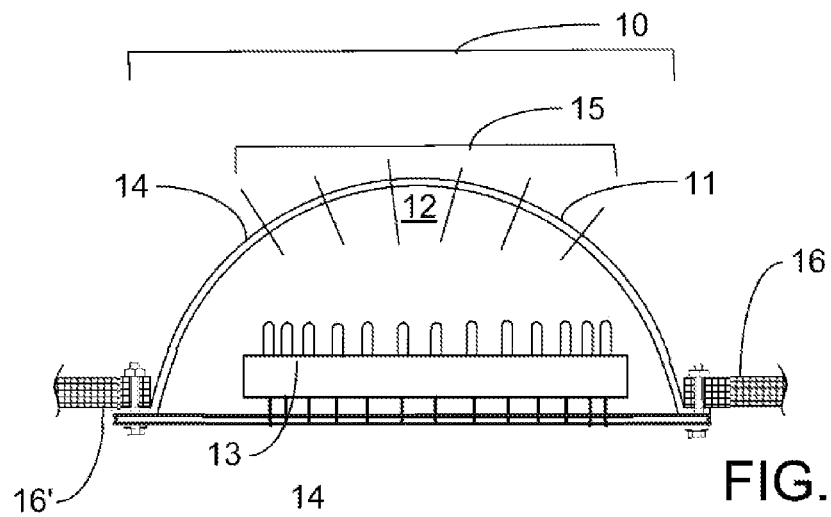
FIG. 1C is a top, cutaway view of the solar grow light LED array of FIG. 1B, encapsulated in a dome window for illuminating the bioreactor vessel.
Figure 1B:
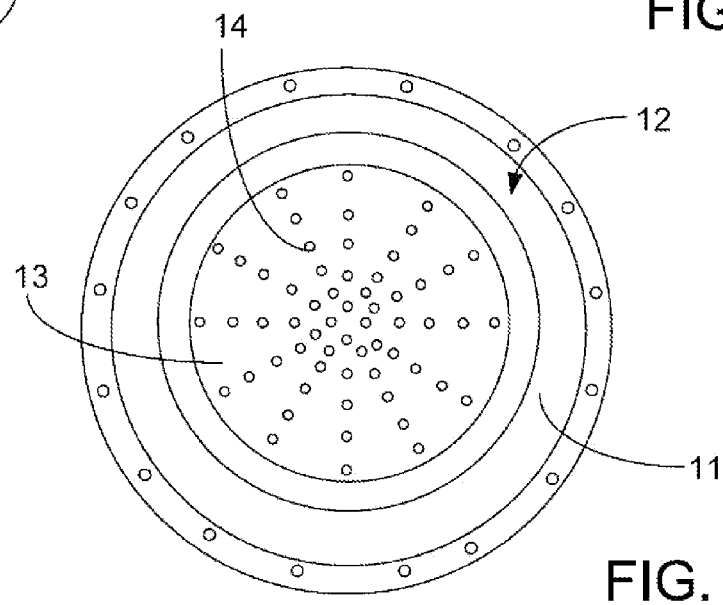
FIG. 1B is a front view of a solar grow light LED array for illuminating the bioreactor vessel.
Figure 1A:
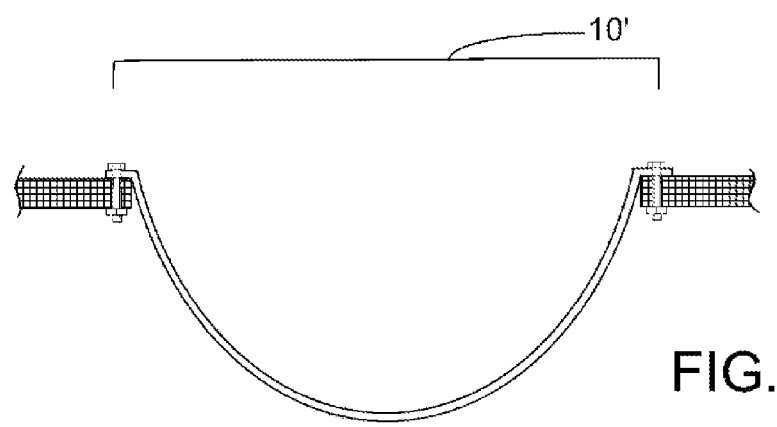
FIG. 1A is a top, cutaway view of a solar port of the present invention engaged to the bioreactor vessel.

Referring to FIG. 1 of the drawings, the exemplary embodiment of the core bioreactor 1 of the present invention is contained by an outer containment vessel 2 having a base 3, and first 4 and second 4', stacked, eight (8) foot tank sections, connected via a 4" flange 5 or lip utilizing threaded fasteners or the like, with a ½ inch thick rubber or elastomeric gasket for a sealed bond, to form a tank having an interior capacity of about 4000 gallons, being about sixteen feet high having lower 6 and upper 6' ends, and a medial 7 section therebetween. As shown, the lower 6 and upper 6' ends of the vessel have a diameter of about seven feet, with the medial 7 section of the vessel at the flange having a diameter of about eight feet. The tank shape, with its medial area having a larger diameter than the upper and lower ends, is designed to promote turbulence in the flow of fluids along its inner wall during operations, as will be further discussed infra.

The first 4 and second 4' tank sections forming the containment vessel 2 are formed of a ½-inch layer of insulating polystyrene foam, which is embedded between a ⅜-inch to ½-inch-thick, spindle-formed fiberglass skin. The upper end 6' of the containment vessel forms an opening which is enclosed via a main dome 8, which dome is formed in the present exemplary embodiment of acrylic, the dome having a ¼ inch thickness and being seven feet in diameter, and having a twenty-four to thirty-six inch rise from the center, with a four inch mounting flange emanating therefrom, the dome may be transparent so as to allow natural solar light transmission into the top of the bioreactor chamber and for observation, or non-transparent depending on the type of millimeter wave energy shielding required. A seven foot diameter mounting ring of high strength, non-steel, composite materials or the like may be provided to secure the dome to the second, upper tank section via threaded fasteners or the like. Also, a millimeter wave shielding laminae may be provided on the surface of the dome to keep millimeter wave or other RF emissions within the bioreactor containment vessel, as will be more fully discussed herein.

Continuing with FIGS. 1 and 1A-1C, the side walls 9, 9' forming first 4 and second 4' tank sections, respectively, have formed therethrough circular openings 10, 10' (in FIG. 1 under the covers 14 shown) for the placement of clear acrylic formed domes projecting into the tanks.

In the exemplary embodiment of the invention, sixteen such domes are provided, each dome 11 being eighteen inches in diameter (although actual size can vary depending upon the type and shape of the artificial lighting apparatus in each application, which may include use as a housing for LED lights or other use), affixed to the inside wall 16 of the tank sections, and can receive LED lights 14 for artificial light, above, or allow natural solar-energy transmission into the tank.

For artificial light, an array of LED lights 14, designed to emit focused, high intensity artificial grow-light energy 15 for photosynthesis into the interior of the bioreactor chamber, is placed in the concave spaced formed in the dome so as to utilize the acrylic dome 11 as an enclosure 12 for receiving a light source 13.

The light source 13 in the present embodiment is mounted to a metal cover 18 which also acts as a heat sink for the heat generated by the LED lights which is engaged to the outer tank wall 16' via threaded fasteners or the like to provide access for outside of reactor light maintenance and inspection, while protecting the light source 13 from weather elements and within the dome 11 enclosure 12 formed by the acrylic dome 11. Gaskets or other sealing materials are provided between the dome 11 and tank wall to prevent fluid penetration into enclosure 12. In the present exemplary embodiment, gasket material is used to seal the top and sides of the round edges of the metal light mounting device which engages the tank wall, with the lower non-gasketed portion left open to the outside of the tank for fan light air circulation.

In addition to the dome LED ports discussed above, twelve inch circular observation panels 63' are provided to the lower and upper tank sections forming the bioreactor, respectively, to allow operators to view the interior of the bioreactor during operation or maintenance, or the like. Also, the lower bioreactor body has formed therein a man-way entry opening with fluid tight entrance panel (made of fiberglass or steel, for example), built into the side to permit access to the interior and sized for allowing personnel to enter the unit for maintenance, cleaning, repair, and otherwise as required.

Each 270-watt LED light system has the energy equivalent of one 1000-watts of metal-halide artificial solar light, resulting in high energy efficiency. The LED lights in the present embodiment are air-cooled by small electric fans that circulate outside air through an inlet 19 formed along the bottom edge of the metal LED light mounting covers (the covers being 20 inches in diameter in the exemplary embodiment).

The present exemplary embodiment of the invention utilizes for the referenced LED light 14 array for the upper, second 4' section of the bioreactor SUPERNOVA, high power LED Grow-light available from HID HUT Inc of Ormand Beach, Fla. 32175. Each unit comprises of 270 watts of high intensity bridge lux LED lights emitting LED Colors Red: 620-740 nanometers (nm) and blue: 405-465 nm, although other grow lights and specification may likewise be used, depending upon the application and operating criteria.

Figure 3A:
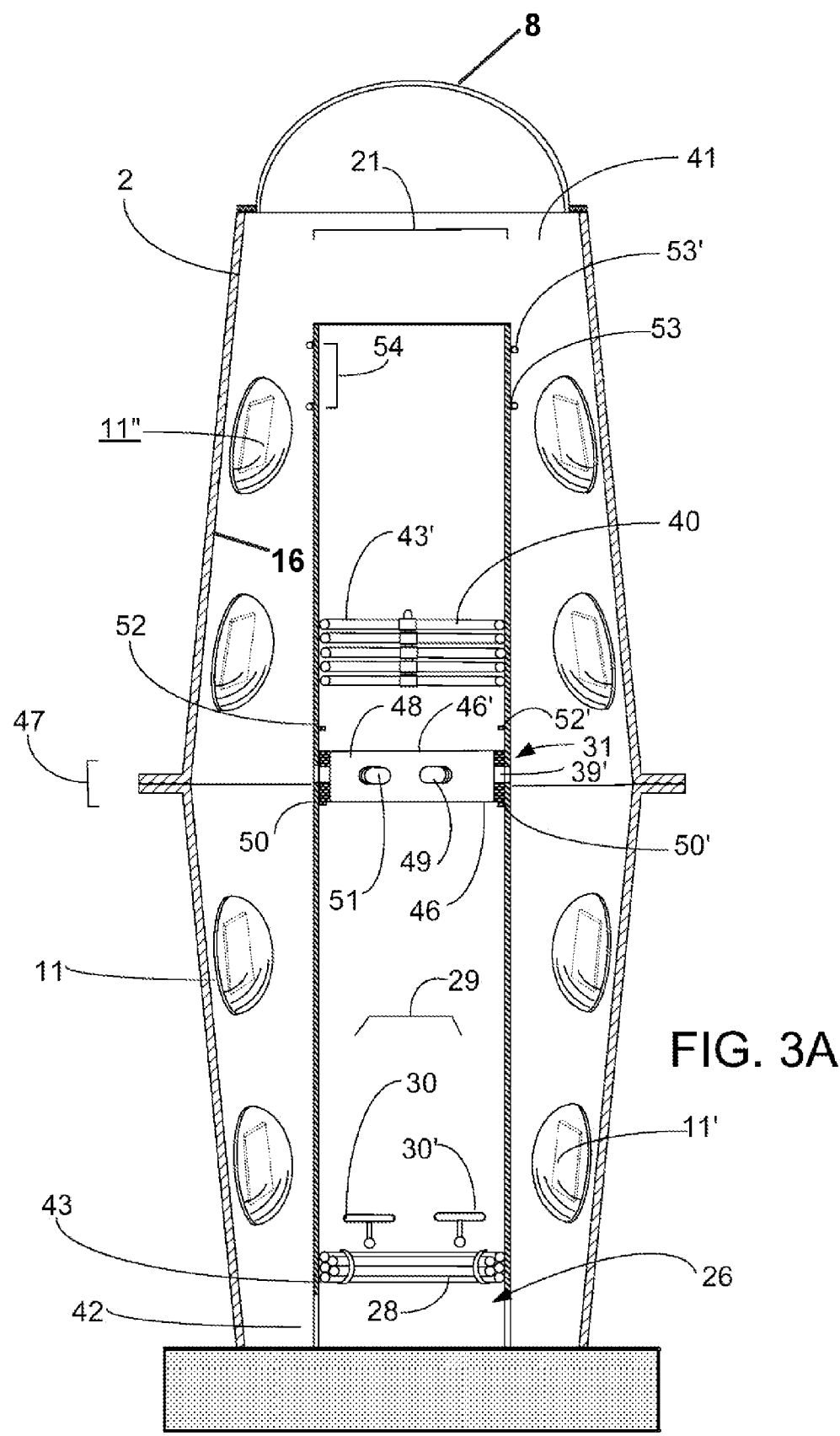
FIG. 3A is a side, cutaway view of the bioreactor flow tube of the present invention, illustrating the lower airlift tubes, the CO2 infusion system, the floating gate valve and the lower airlift tubes, as enclosed by the bioreactor vessel of FIG. 1.

Continuing with FIGS. 2 and 3A and B, a bioreactor flow tube 22 having a longitudinal passage 37 therethrough, a length 20 of about fourteen feet, and an outer diameter 21' of about four feet, is situated within the bioreactor containment vessel 2 of the present invention. The flow tube 22 may be fabricated of PVC pipe or fiberglass materials, having a first 23, lower and second 23' upper open ends, with a medial portion 24 therebetween, and passages 39, 39' formed laterally through the medial portion 24 in spaced fashion about the diameter of flow tube 22.

The first 23, lower end of flow tube 22 has formed through sidewall 17 lower flow cutouts 26, 26' forming legs 43 to support the tube 22 vertically on the base 42 of the containment vessel 2, the cut outs 26, 26' also providing an opening for the flow of fluid from the containment vessel 2 into the first 23 lower end of tube 22 for recirculation, as will be further described herein.

Figure 3B:
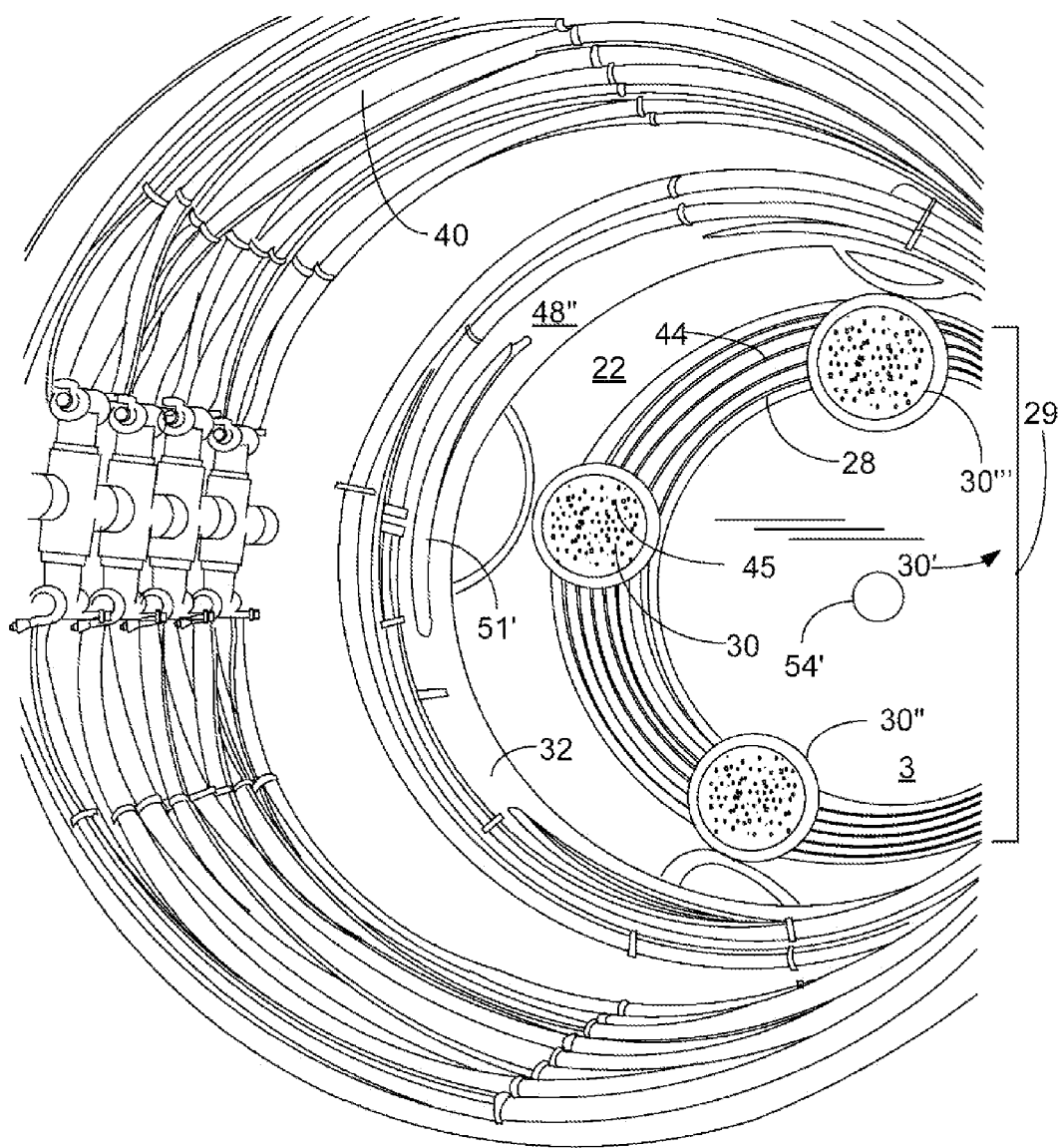
FIG. 3B is a top, perspective view of the bioreactor flow tube of the present invention, illustrating the upper airlift tubes, the floating gate valve, the lower airlift tubes, and the CO2 Infusion system.

FIGS. 2, 3A and 3B illustrate the vertically situated flow tube 22 centered within the interior 41 of the containment vessel 2, with the first 23, lower end of tube 22 situated on support base 42, the flow tube in the present exemplary embodiment being four feet in diameter, ¼" wall thickness, and fourteen feet in length.

As shown, within the flow tube near the first 23, lower end, but above cutouts 26, 26' is a coil 43 of one inch diameter perforated air hose forming a lower airlift tube 28, said coil aligned with and mounted to the inner diameter 21 of flow tube in six loops from a header system fed by an air supply line from a small, 2.5 HP regenerative air blower. The exemplary embodiment of the present invention utilizes SIEMENS brand FLEXLINE™ fine bubbler (also referenced as micro bubbler) diffuser hose, providing an energy efficient, air-lift system for maintaining a continuous, slow movement of the growth medium solution within the maturation chamber of the reaction vessel, as will be more fully shown below.

Centrally situated in the base 3 of the bioreactor is the growth medium (bloater) return port 54' (for return of material into the bioreactor after monitoring or processing), or be selectively used to drain the system.

Situated within the flow tube and spaced above the lower airlift tube 28 are four ceramic, round, fine-bubble air diffusers 30, 30', 30", 30"' connected to one another via circular hose 44 to form a CO2 or other gas infusion array 29, each of diffusers situated generally equally spaced from one another to form an upwardly facing ring of diffusers, the outer periphery of which is adjacent to the inner diameter 21 of flow tube. Each of the four diffusers 30, 30', 30" and 30"' include a 10-inch-diameter fine membrane 45 for diffusion of CO2 or other gases into the base of the bioreactor flow tube for control of pH, for example; this gas delivery system can also be used to infuse other forms of gas treatments including compressed air, as will be further disclosed infra. The diffusers of the present embodiment of the invention are SIEMENS brand FLEXDOME™ fine bubble diffusers.

Spaced above the CO2 infusion array 29, in the medial portion 24 of the flow tube (in the present case, about 7 feet from the lower, first end 23 is a floating gate valve 31 comprising a ring body 32 having first 46 and second 46' ends defining a length 47, an outer diameter 48 and inner 48' diameters. The ring body 32 is formed of a cylindrical surface 49, the outer diameter 48 of which is slightly less than the inner diameter 21 of the flow tube so that said ring body may slidingly engage the inner diameter of same.

The ring body 32 is preferably formed of a material which has a positive buoyancy in water or other liquid in use, and is formed to rest upon lower stops 50 affixed to the inner diameter of the flow tube, which stops positioned to support the first, lower end of the ring body, when the system is not operational or when there liquid in the system is about half or less level.

The cylindrical surface of the ring body 32 has formed therethrough flow apertures 51, 51' situated to be aligned with passages 39, 39' formed medially in the flow tube 22 when the ring body 32 is resting on lower stops 50, 50', to provide medial flow through the flow tube structure, while upper stops 52, 52' are provided in spaced fashion above the lower stops so as to position the ring body to close the flow through the medial flow passages 39, 39' when the ring body is in its floating, upper position, as will be more fully discussed infra.

Situated within the interior diameter 21' of the flow tube 22, preferably just above the medial portion 24 of said tube, is the upper airlift tube 40, formed of a ring 43' or coil of one inch perforated air hose in general alignment with and adjacent to the inner diameter of flow tube 22, and configured to disperse air into the upper inner diameter of the flow tube during operations at full water level, as will be discussed herein.

In the present exemplary embodiment of the invention, the upper and lower air lift systems are identical in construction and uniquely spaced apart so that the small (in the present example, 2.5 HP) regenerative air blower providing the air thereto can overcome the head pressure of the liquid within the core bioreactor, whether half full (using only the lower air lift) or completely full (using only the upper air lift), thus minimizing energy expenditures for operation. In the present case, the upper airlift tube comprises six loops of a special energy efficient micro bubbler air hose, same as the lower air lift, the SIEMENS brand FLEXLINE™ fine bubbler air hose, and is powered via the same 2.5 HP regenerative blower (exterior the bioreactor) as the lower air lift.

Energy efficiency is extremely important as to the commercial viability of enclosed photobioreactor systems, and the present airlift design greatly adds to the efficiency of the present system, as well as providing a major operating cost advantage over the prior art.

Situated about two feet from the upper, second end 23' of the flow tube is an electromagnetic coil device in the form of a Helmholtz coil, comprising first 53 and second 53' electromagnetic coils spaced 54 or otherwise situated about 24.5 inches from one another, to selectively provide an electromagnetic field, as will be further explained herein.

In the preferred embodiment of the invention, the interior wall 53 of the flow tube forming the inner diameter 21 is of a black or other light absorbing color to provide a dark interior, while the outer wall 53' forming the outer diameter 21' of flow tube has a light reflective coating, such as a mirror or metallized silver coating, using, for example, metallized MYLAR brand film or the like, the reflective finish formed to reflect and scatter the natural and artificial solar energy emitted through the upper EMF dome and 16 transparent domes 11, 11', 11" with LED grow light arrays mounted therein (see FIGS. 1B & 1C) within the interior 41 of the containment vessel 2 of the bioreactor.

Further, the interior wall 16 of the containment vessel 2 has applied thereto a bright metal, reflective finish, in the exemplary embodiment of the present invention, utilizing CIBA brand METASHEEN™ finish, a VMP pigment slurry composed of 10% lamellar, non-leafing aluminum flakes dispersed in ethyl acetate. Further, the reflective coating can be applied to the inside of the main dome 8 where it is impractical or undesirable to have natural sunlight pass through the dome 8. By providing reflective material on the outer wall of the flow tube and the inner wall of the containment vessel, an enhanced reflective light chamber is formed in the annular area between the outer walls of the flow tube 22 and the inner walls 16 of the containment vessel 2.

To further enhance the reflection of the inner walls of the containment vessel 2 (and the dome if a reflective finish is desired) glass beads are used to create a multi-directional, highly reflective and salt water durable coating upon the underlying reflective finish. The beads are 12/20 mesh size, evenly applied ¼ pound per square foot of the surface area applied as follows. The reflective finish is applied to the inner wall of the containment vessel 2 (and elsewhere as desired) by applying a mixture of clear marine grade epoxy, mixed with METASHEEN™ finish. While the epoxy is still tacky, the 12/20 mesh size glass beads are sprinkled with a "salt shaker" like device evenly over the wet epoxy surface, in the ¼ pound per square foot of surface area as discussed to provide an even dispersion. The beads adhere to the wet epoxy and once it cures, a highly reflective silver mirror surface which will effectively reflect and disperse the intensive grow-light lightwaves provided therein, which is reflected off the MYLAR mirror finish of the centrally located flow tube.

Specifics on the glass beads follows: airport grade glass beads for topical application 12-20 mesh (0.84-1.68 mm), 10 lbs—glass beads for topical or intermix applications 30-50 mesh (030.059 mm).

The dual reflectivity of the outer flow tube, on one side, and the inner walls of the containment vessel, on the other, combined with the high intensity LED light arrays projected therein, and the turbulent flow of the photoautotropic organism therethrough provides an enhanced light exposure chamber which, when utilizing a UV filtered main dome for natural light exposure coupled with the artificial light: a) takes advantage of improved sidelighting, b) increases the surface area illuminated, c) drastically reduces photosynthetic saturation, d) demonstrates the ability to achieve much higher volumetric carbon fixation rates, e) filters unwanted UV and iR radiation from the bioreactor, f) minimizes heat delivery, and e) increases the overall sunlight utilization efficiency and cost-effectiveness when compared to earlier photobioreactors.

Referring to FIGS. 1, 2, and 3A-3C in the first stage of operation of the present invention for forming algae or the like, a growth medium solution with the algae and added water forming a liquid suspension 57 is provided with the start up fluid level 55 filling about one half of the bioreactor (the "start up" stage) so that the gate valve 31 is not lifted by the liquid, and remains at its lower stage resting upon lower stops 50, 50', the water level being about even with the medial flow passages 39, 39' formed through the sidewalls of the flow tube 22.

UV sterilized, filtered air is urged from a blower via hose to lower airlift tube 28 so that air bubbles 56 emanate therefrom to form in the surrounding liquid suspension 57, which air bubbles float upward, urging the liquid suspension within the flow tube 22 to flow 58 upward, with the liquid suspension flowing in 61 through the lower flow cutouts 26, 26', which upward flow 58 reaches start up water level 55, where the bubbles are released into the air above water level 55.

The flow at water level 55 then passes 59 through the gate valve flow apertures 51, 51' and the aligned flow tube 22 medial flow passages 39, 39', where it flows downward 60, encountering domes 11, 11', which create turbulence within the system so to allow a mixing effect of the algae in suspension to become exposed to the grow-light energy 57, while preventing settling of the algae suspended therein. These microscopic plant-like organisms require only milliseconds of exposure to specific grow-light wavelengths for cell division to occur which will be provided by the reflective exterior of the flow tube bouncing the high intensity LED light energy back and forth from the reflective finish of the interior reactor wall thus creating a light chamber to maximize grow-light exposure to the algae as they circulate through the illuminated chamber.

The flow through the gate valve 31 and medial flow apertures 39, 39' through the flow tube is necessary for startup to provide liquid suspension/bloater circulation over the LED solar grow lights in domes 11, 11' in the lower half of the bioreactor containment vessel, since algae organisms require concentration of cell count during organism maturation, and prior to dilution into larger growing volumes.

As a result, typically the entire 4000 gallon bioreactor cannot be fully loaded with liquid suspension 57 during the initial organism growth start-up period. Therefore, only the lower half of the bioreactor is used to allow sufficient time to concentrate the algae population before adding additional liquid and nutrients to raise the fluid level to the top of the bioreactor, where either natural solar light or millimeter wave energy stimulation is provided for photosynthesis through the 7 foot diameter, acrylic dome located on the top of the bioreactor, as well as through the exterior flat panel photobioreactor, further described herein.

During operation, the liquid suspension 57 is monitored for algae concentration, purity, PH, CO2, Oxygen and algae nutrient levels, salinity (where salt water species are cultivated), as well as other factors. The PH is adjusted via the use of a PH monitoring/probe and control device that controls an electric valve that atomically allows the injection of CO2 gas into the system by an external air control and filtration system which sterilizes and mixes ambient air, and blows the mixed gasses into the micro bubble diffusers 30, 30', 30", 30" and or through the lower 28 and upper 40 air lift tubes. Either of the three air/co2 delivery systems (exemplary embodiment of the micro-bubbler type) can add CO2 to the system for 24/7 automatic PH control. PH may also be adjusted via known chemical additives.

Figure 3C:
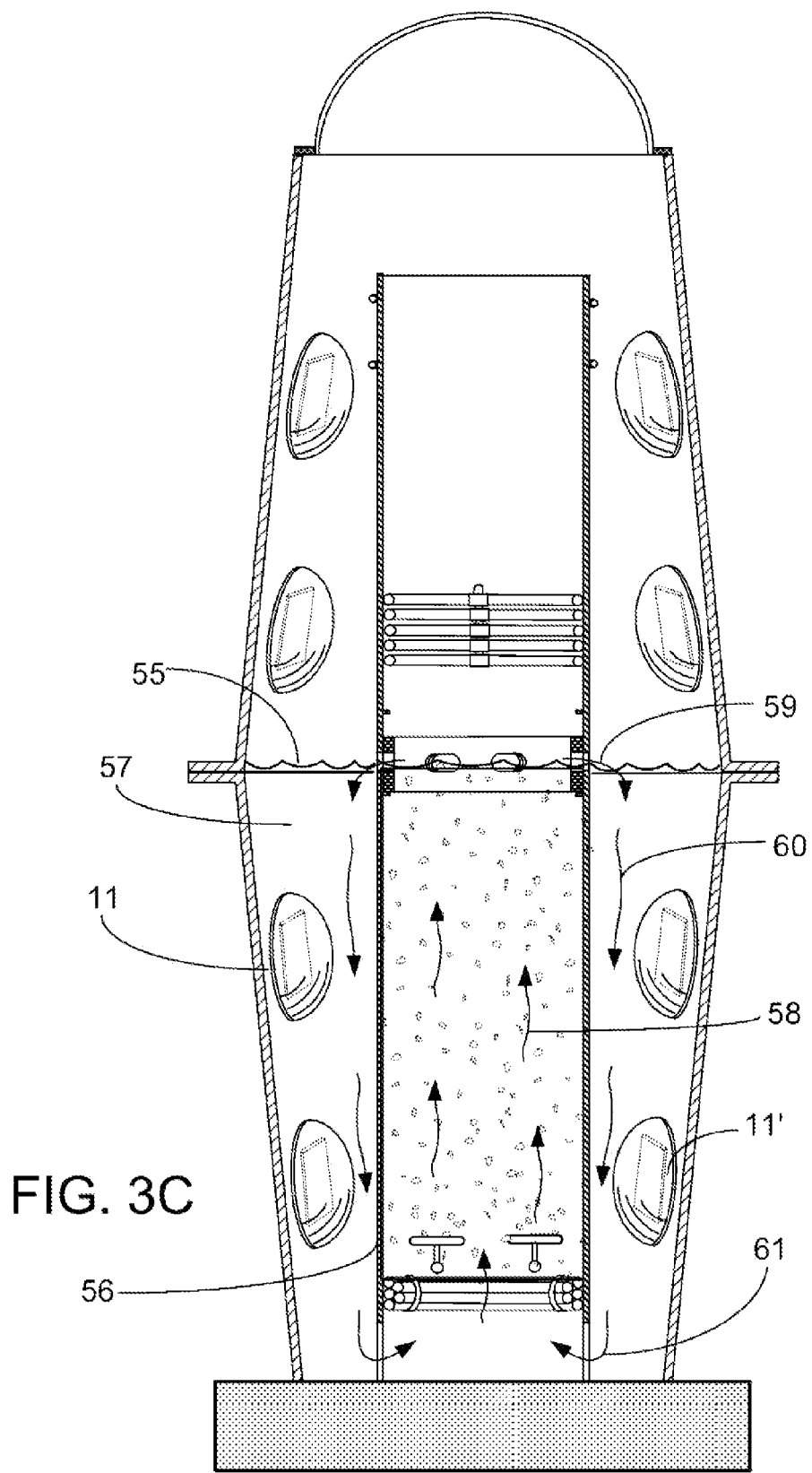
FIG. 3C is a side, partially cutaway view of the bioreactor vessel of FIG. 3A half filled with fluid, with the sliding gate valve in the lower, open configuration, with circulation occurring through the medial flow apertures formed through sidewall of the bioreactor flow tube, and the operation of the lower airlift tube and CO2 infusers, as contained by the bioreactor vessel of FIG. 1.
Figure 3D:
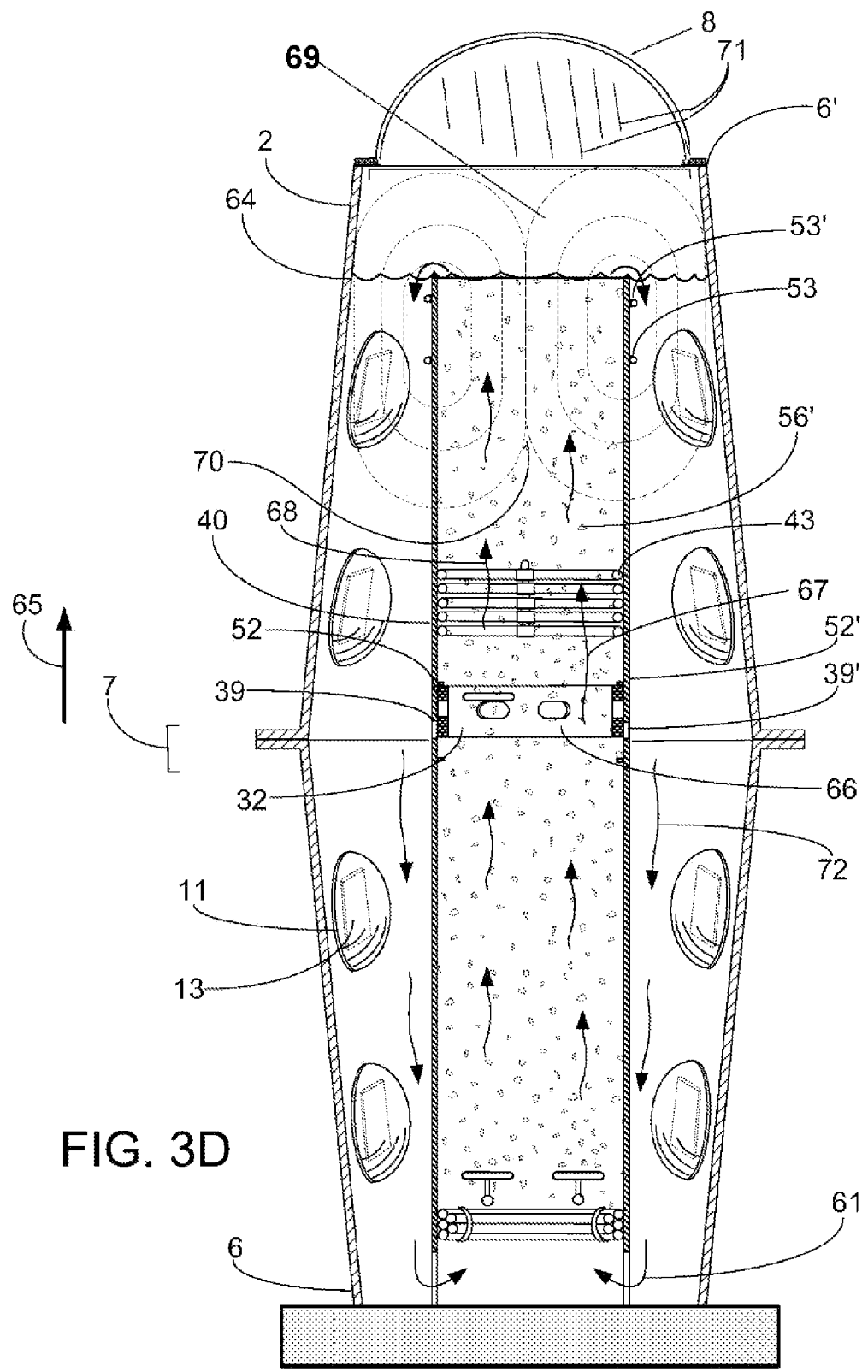
FIG. 3D is a side, partially cutaway view of the bioreactor vessel of FIG. 3A fully filled with fluid, with the floating gate valve in the floating, upper, closed configuration to prevent flow through the medial flow apertures formed in the flow tube, with circulation occurring through the top of the flow tube, and the operation of the lower airlift tube, upper airlift tube, and CO2 infusers, as contained within the bioreactor vessel of FIG. 1.

Once the FlowCam™ monitoring equipment has detected sufficient algae concentration, the fluid level with nutrients and other additives may be raised to full fluid level 64, and full bioreactor operating status, as illustrated in FIG. 3D.

Continuing with FIGS. 1, 1C, 2, and 3A-3D, once the water level raises above the mid point fluid level 55 denoted in FIG. 3C (in this case, over 7 feet and higher than the medial flow apertures 25 in flow tube 22), the ring body 32 forming the gate valve is lifted 65 by its buoyancy in the rising liquid, lifting the ring body 32 from its resting position on lower stops 50, 50', floating upwards until the ring body 32 is stopped from further rising via upper stops 52, 52'. At the upper stops 52, 52', ring body 32 is positioned so that the space 66 in the ring body between the flow apertures 51, 51' and lower, first end 46 of the ring body blocks medial flow apertures 39, 39', blocking the flow of fluid therethrough, allowing the fluid in the flow tube 22 to flow through 67 the ring body 32.

Once the fluid level rises above the upper airlift tube 40, air flow is initiated through the ring 43' or coil of perforated air hose forming same, replacing the air flow from the lower airlift tubes 28 as earlier discussed, the upper airlift tube 40 airflow further dispersing air bubbles 56' into the upper inner diameter of the flow tube to further enhance the air lift 68 action and enhance upward fluid circulation within and out of the upper, second end 23' of the flow tube.

After passing through upper airlift tube 40 (preferably micro bubbler as earlier indicated), the liquid suspension including algae passes through the earlier discussed first 53 and second 53' electromagnetic coils forming the Helmholtz coil.

During algae growth operations at full tank level (as shown in FIG. 3C), the Helmholtz coil is energized to produce a homogeneous magnetic field 69 approximately aligned with the central longitudinal axis 70 of the bioreactor flow tube 22', and extending outward to at least the inner walls of the bioreactor containment vessel 2, which may have electromagnetic shielding in place to prevent the field from extending out of the bioreactor.

A uniform, low frequency magnetic field that charges the water molecules with energy which, at low energy levels, transfers into stimulating cellular growth, or at higher energy creates cell lysis (splitting the cell wall) for the oil/cellulose separation operation, described in the general summary discussion of the invention, supra.

For use in improving the cellular growth rate, the electromagnetic field strength generated by the Helmholtz coil device is expected to operate between 15 and 100 Hz at 2 ut, 4 ut, 6 ut, 8 ut up to 100 ut.

Once the air lifted algae biomass has flowed through the Helmholtz coils located in the top portion of the darkened flow tube 22, it is exposed to natural sunlight 71 from the main dome 8, or an artificial growing light can be provided, when required to project from the dome area (example the upper side of the dome) into the containment vessel.

The algae with water then flows over the upper second end 23' of the flow tube, then encounters downward flow_72 due to siphoning action due to flow 61 through the lower flow cutouts 23, 23' in flow tube 22, caused by the lifting action from upper 40 air lift within the tube 22.

As mentioned above, during this period of flow downward from the upper end 23' of the flow tube 22 to the lower end 23, the algae is exposed to artificial grow light from the many LED's situated in the acrylic spheres along the length of the bioreactor containment vessel, which light is reflected off the outer reflective surface of the flow tube, providing an enhanced grow light chamber with turbulence generated by the uneven inner surface of the containment vessel 2 due to the many domes 11 housing the LED sources 13.

In addition, the shape of the bioreactor containment vessel 2, with its earlier discussed wider medial section 7 than lower 6 and upper 6' ends causes further turbulence within the reactor as created by the air-lift system as it pushes out of the flow tube (either medially or out of the top, depending upon the water level), then down along the length of the outer containment vessel.

The algae and liquid suspension continues to be drawn downward along the interior wall of the containment vessel 2 and exterior the flow tube 22 as it continues to be exposed to the enhanced grow LED lights, until the algae and liquid suspension reaches the bottom of the bioreactor, where it is drawn through 61 the lower flow cutouts 26 of the bioreactor flow tube 22, and into and up the dark interior of the lower flow tube, wherein the algae "rest" (in the dark) as it travels up the length of the interior of the flow tube, (where it may be again exposed to an EMF field via the Helmholtz coil if desired), ultimately flowing out of the top of the flow tube, from dark to light, where the algae is again drawn down the exterior of the tube and exposed to the artificial and/or natural sunlight, with the cycle repeated.

Figure 6A:
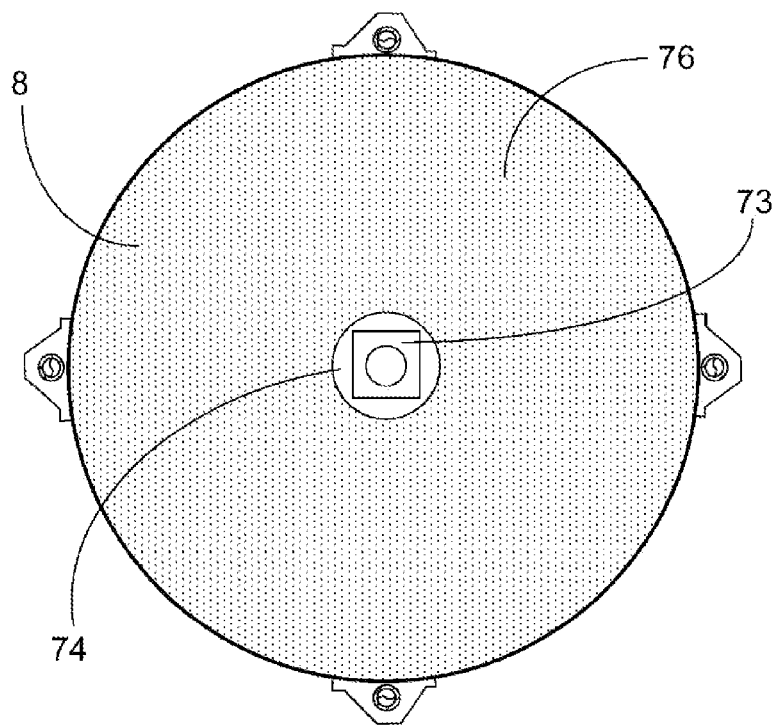
FIG. 6A illustrates a top view of the acrylic dome of the bioreactor vessel of FIG. 6A.
Figure 5:
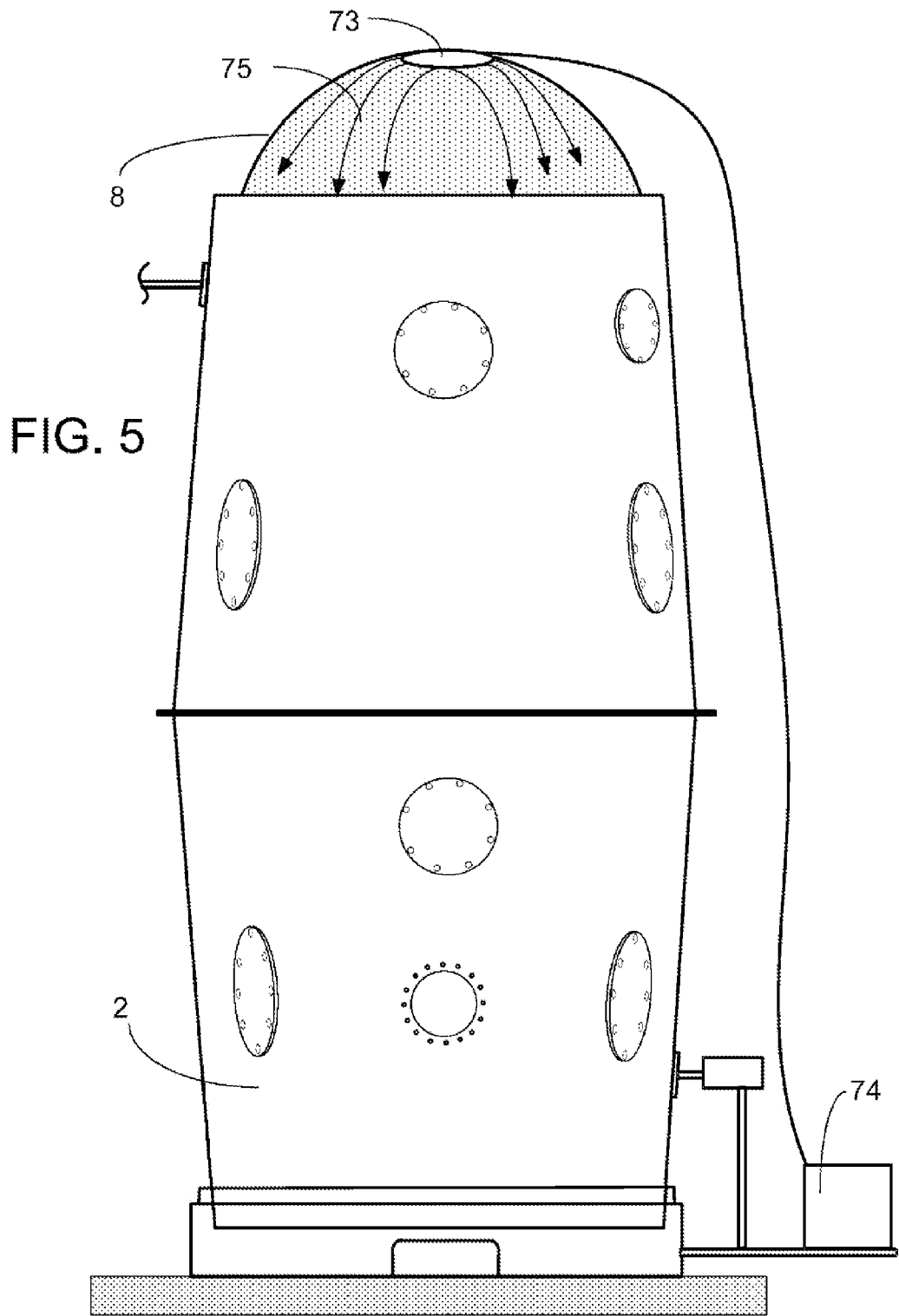
FIG. 5 illustrates an alternative embodiment of the present invention wherein there is provided a millimeter wave emitter in the dome area of the main core bioreactor formed to beam millimeter waves into the headspace at the top of the bioreactor.
Figure 6:
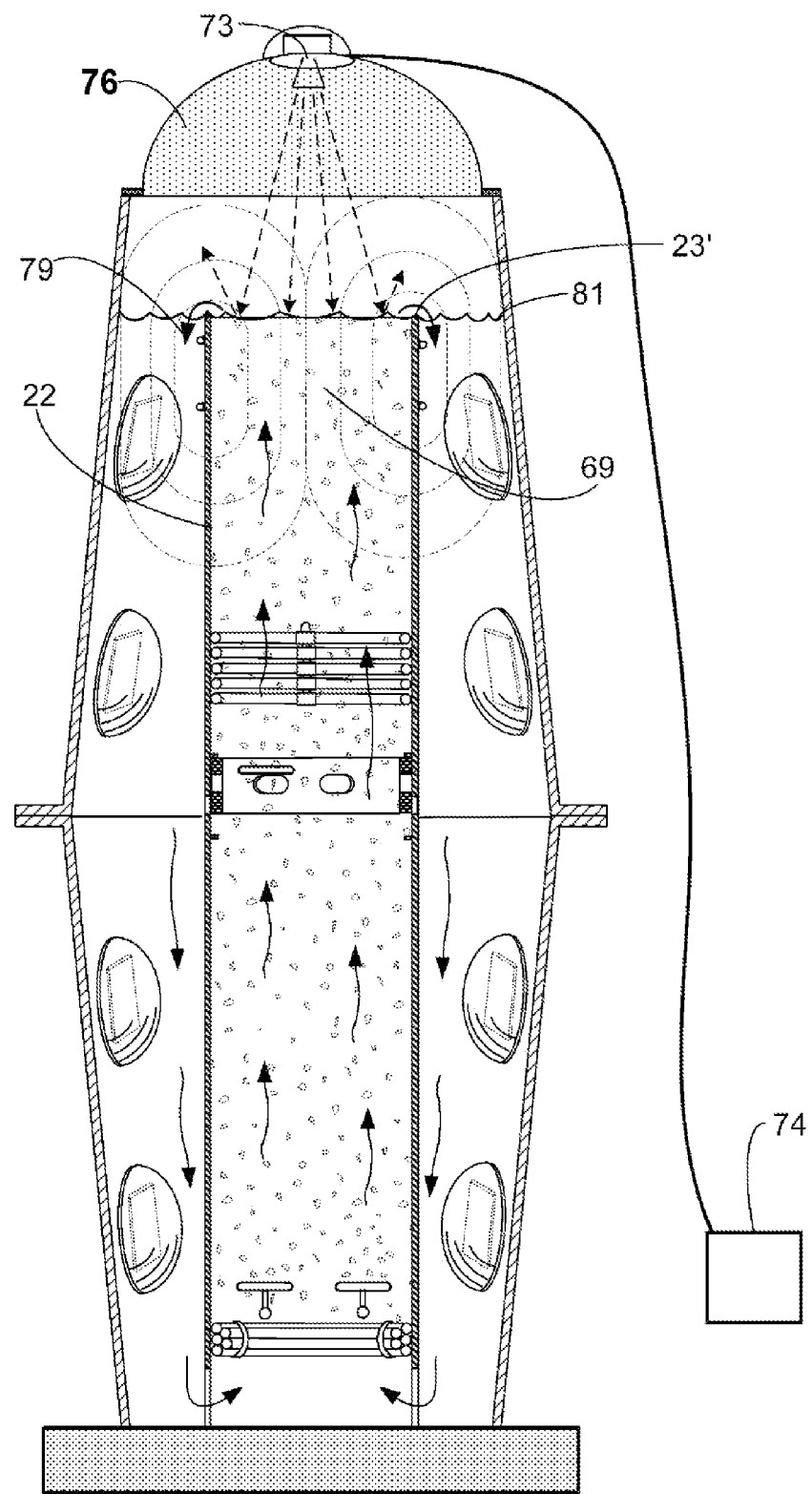
FIG. 6 illustrates the mounting and operation of a millimeter wave emitter mounted on the main dome of the bioreactor.
Figure 7:
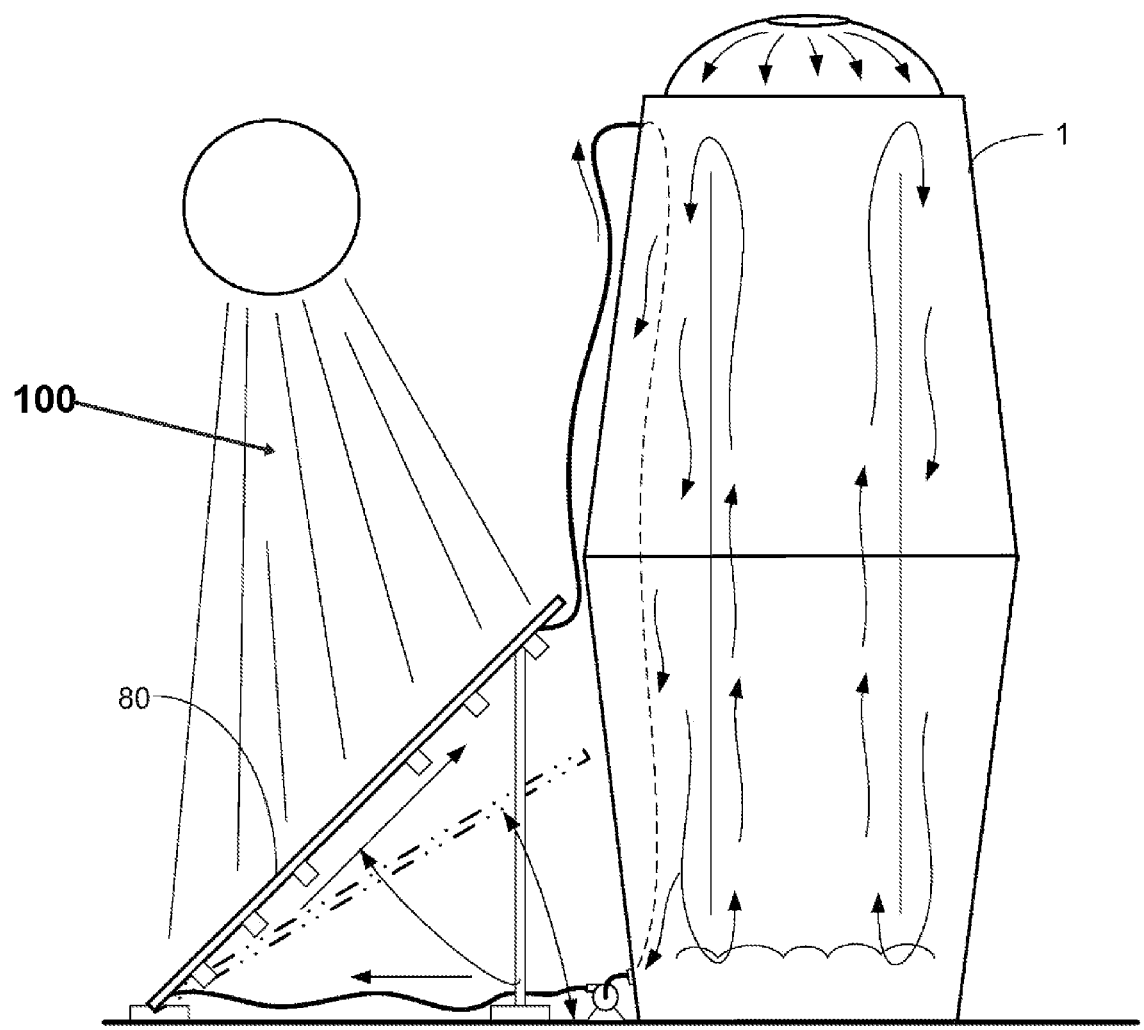
FIG. 7 illustrates a side view of an exterior flat bioreactor panel having LED grow light capability engaging the bioreactor (flow tube shown in phantom) of FIG. 1.
Figure 8A:
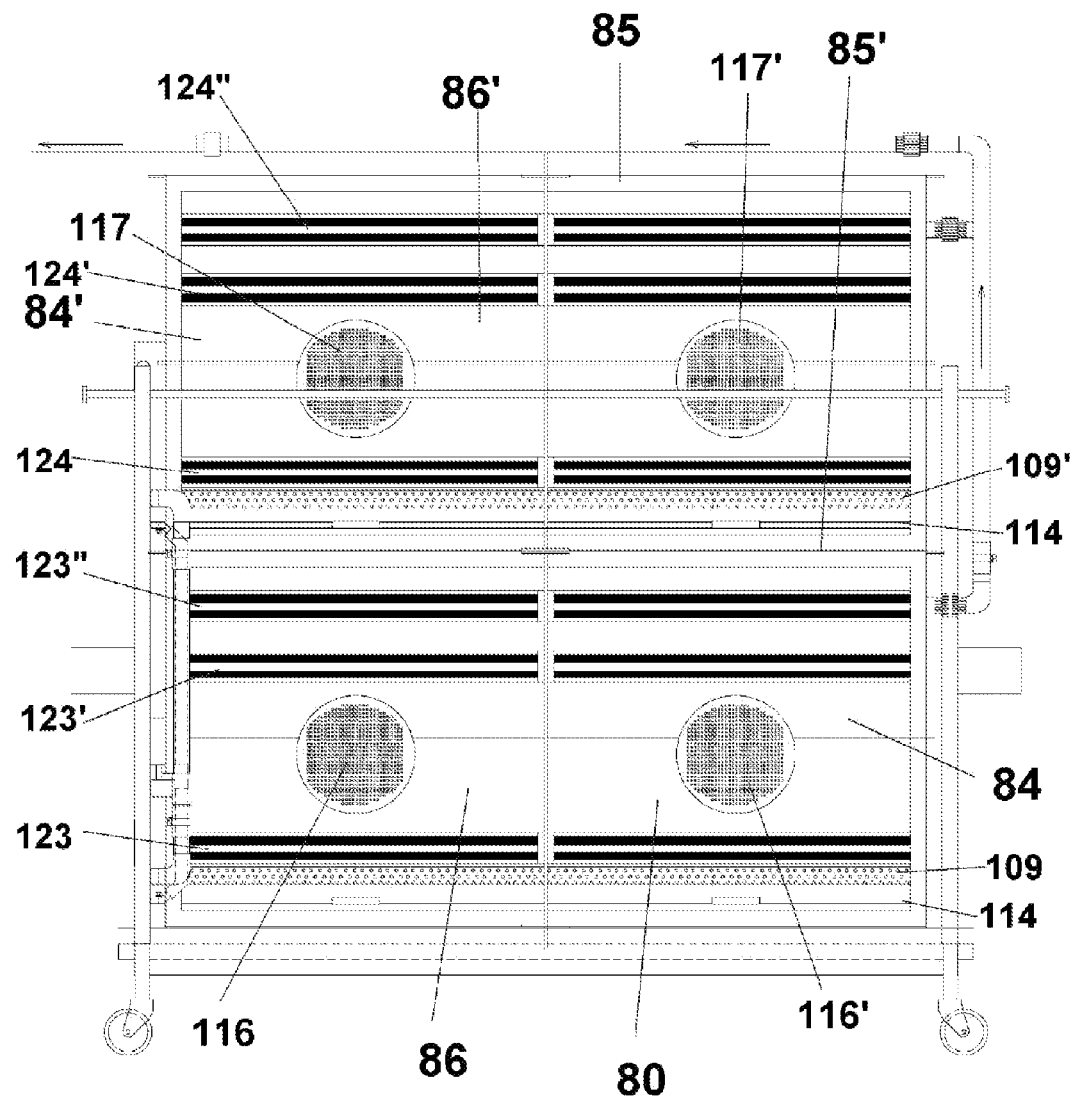
FIG. 8A is a front, partially cutaway view of the bioreactor panel of FIG. 7.
Figure 8B:
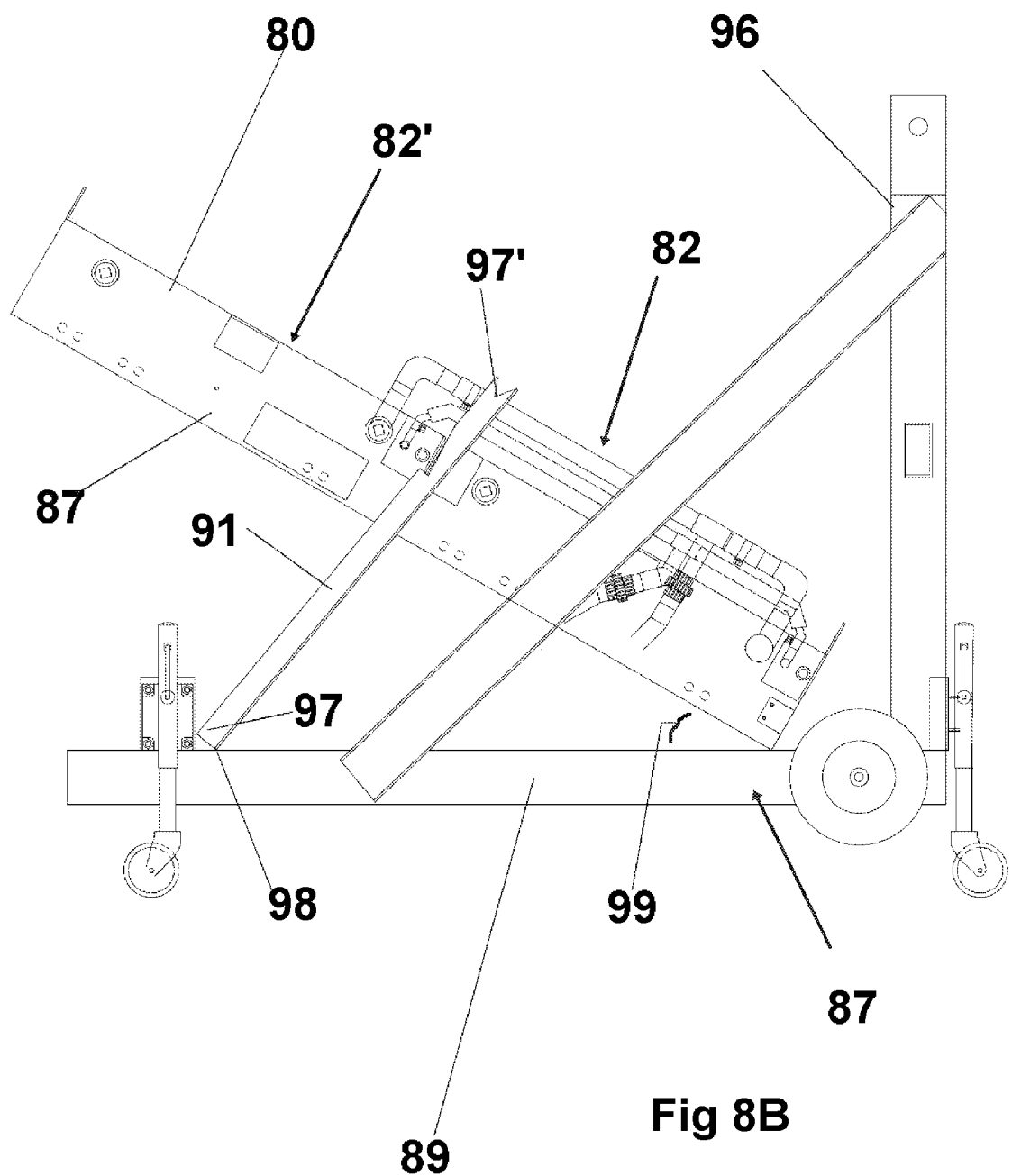
FIG. 8B is a side view of the bioreactor panel of FIG. 7.
Figure 8D:
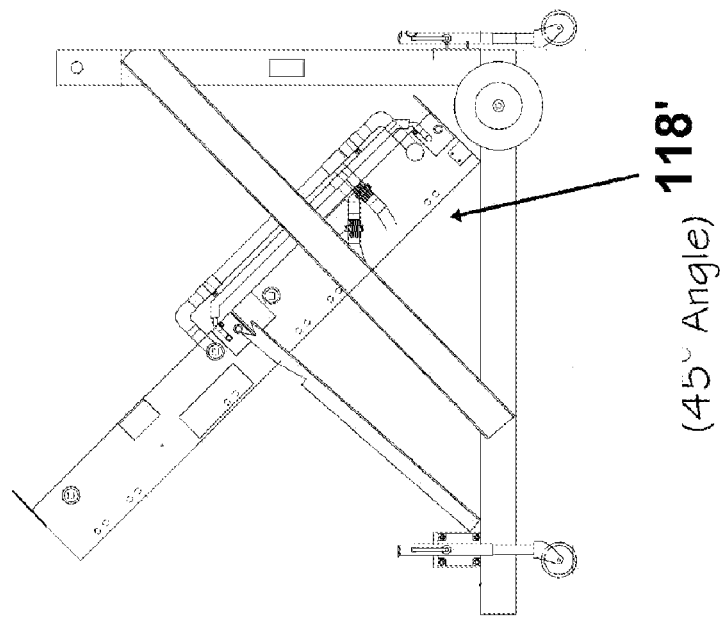
FIG. 8D is a side view of the bioreactor panel of FIG. 7 at a forty-five degree angle.
Figure 8C:
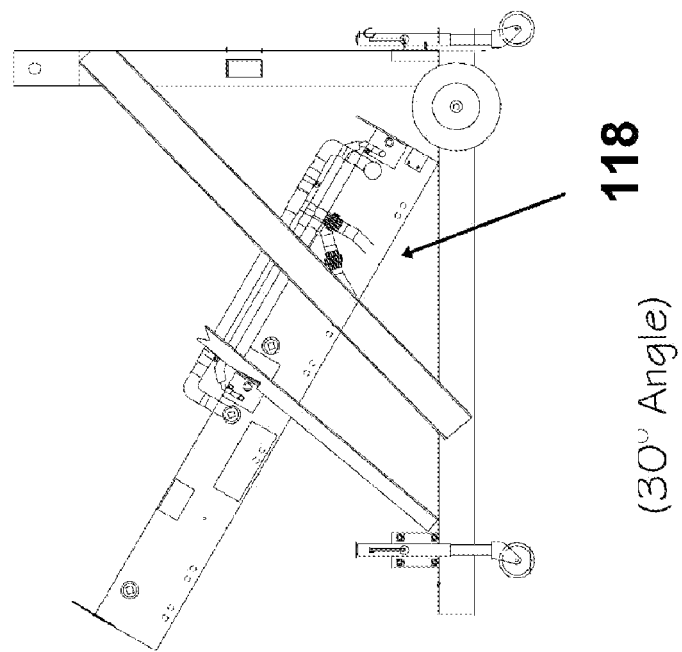
FIG. 8C is a side view of the bioreactor panel of FIG. 7 at a thirty degree angle.
Figure 9:
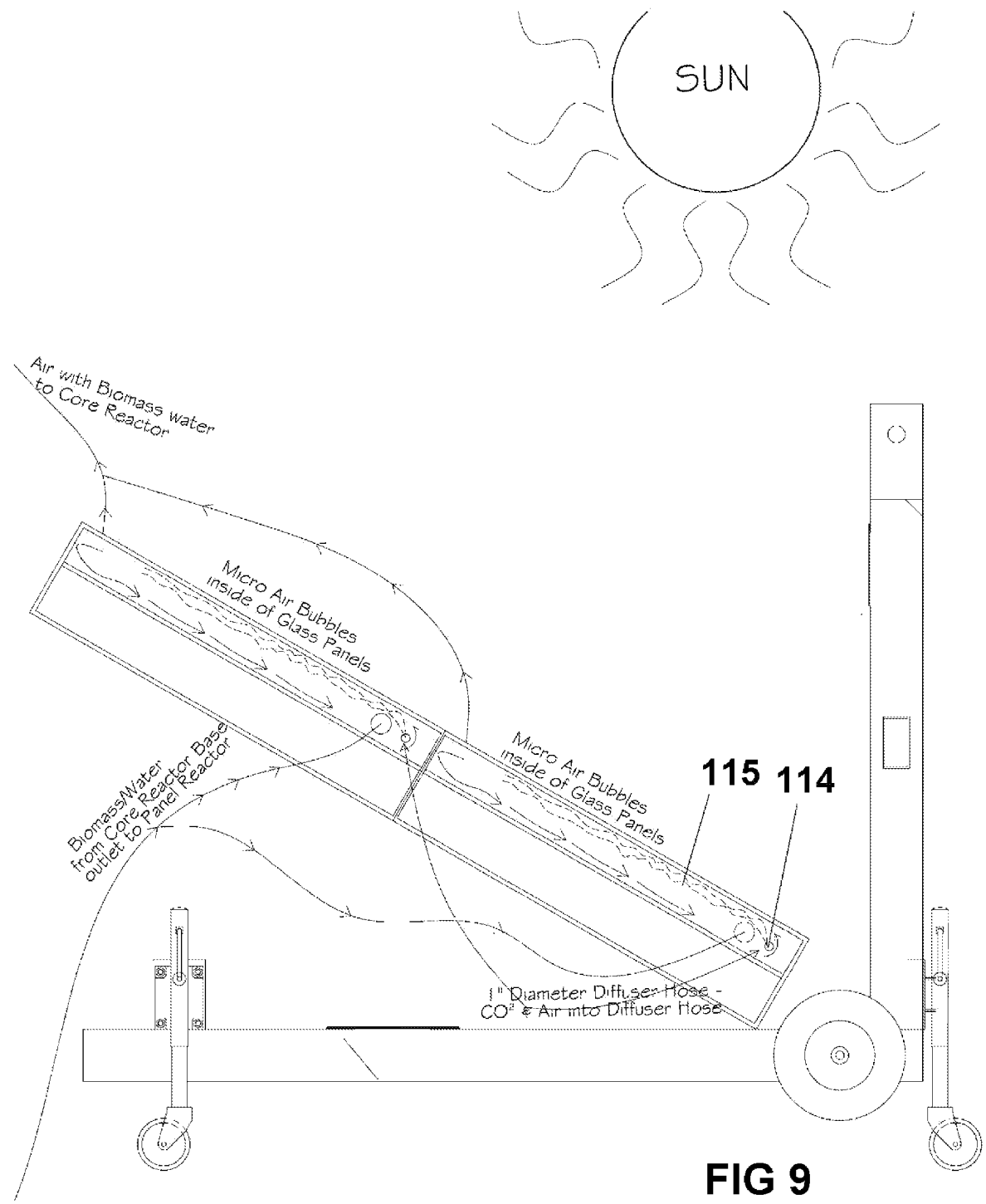
FIG. 9 is a side, partially cut-away view of the flat panel bioreactor of FIG. 7, illustrating the circulation of air bubbles therethrough.
Figure 9D:
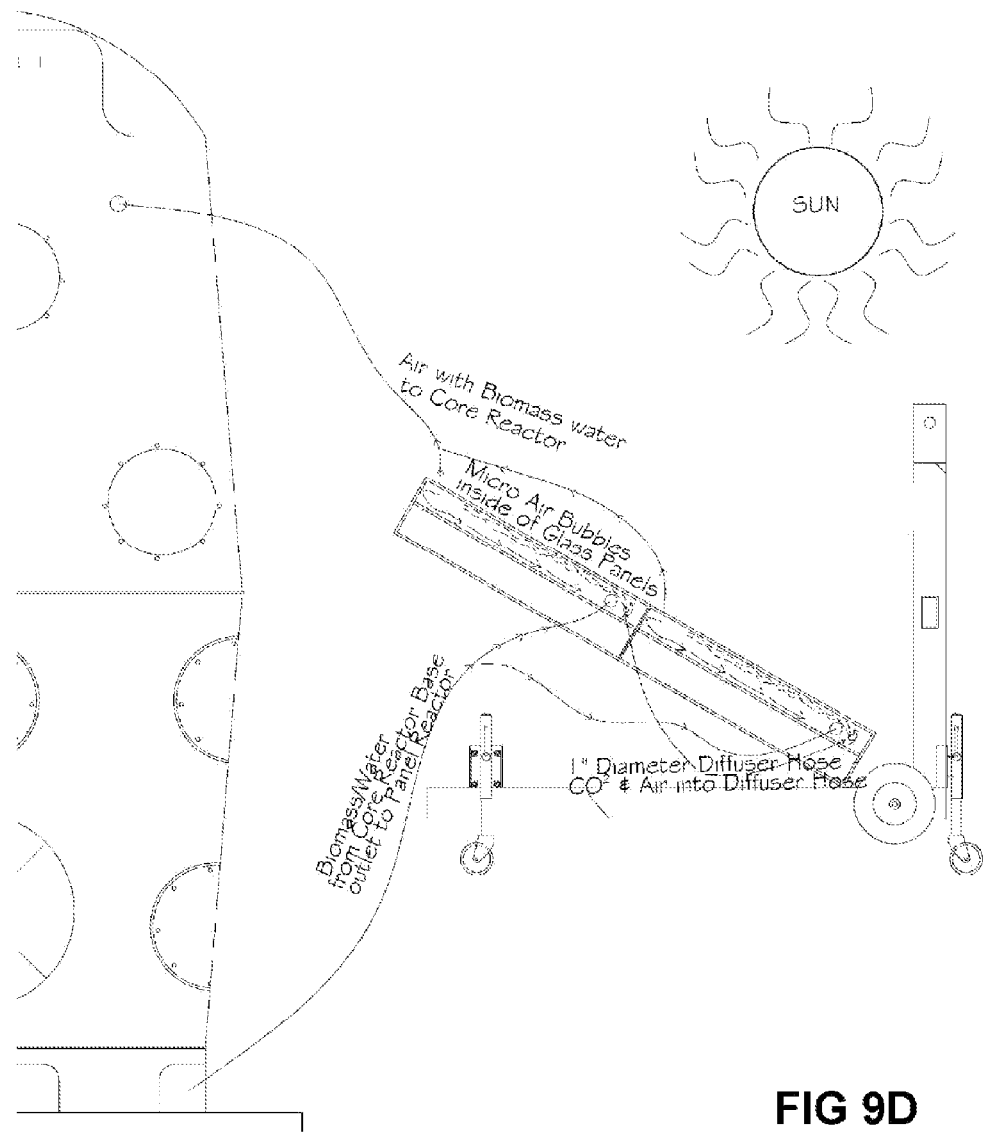
FIG. 9D is a side, partially cut-away view of the flat panel bioreactor of FIG. 9, illustrating the flow of the unit from and to the core bioreactor to support same.

Continuing with FIGS. 5, 6 and 6A, in addition to the Helmholtz coil system described above, the present invention may include a tunable millimeter wave generator 74 with a concomitant wave guide transponder/antenna 73 associated with the top center of the reactor dome, to provide within the reactor a controlled tuneable millimeter wave electromagnetic radiation 75, which is beamed to the water surface level 81, where it penetrates the surface to generate the stimulation of cell division (mitosis) by enhancing the regeneration cycle of the algae. Examples of known millimeter wave emitters which may be suitable for this purpose may include traveling wave tubes including a backward wave tube also known as a backward wave oscillator (BWO) or carcinotron; other millimeter wave sources including other vacuum tubes may also be suitable.

The millimeter wave emitting antenna 73 is situated in the center vicinity of the acrylic dome associated with the top of the core bioreactor (that is, within the dome inside the bioreactor or mounted outside the dome), and configured to emit a special frequency EMF millimeter wave with exposure times that may vary from 20 minutes per day to 24 hours per day, dependant upon the cell-division rate.

To contain the EMF wave within the bioreactor containment vessel 2, a layer of EMF wave reflection and shielding material 76 should be laminated to the inside of the acrylic dome surface as well as the upper portion (from about one foot below the water line to the top) of the upper, second 4' section forming the containment vessel. Preferably, the EMF shielding and reflection material 76 associated with the dome 8 is formed of material which allows the passage of natural or artificial light energy associated with photosynthesis therethrough.

The unique configuration of the present bioreactor design is such that the algae and growth medium exiting 79 the upper, second end 23' of the bioreactor flow tube is briefly situated at the upper water level 81, and as such is briefly exposed to the millimeter wave electromagnetic radiation 75.

It is noted that, although FIG. 6 illustrates the operation of the Helmholtz coil electromagnetic field 69 (FIG. 3C) and the millimeter wave field 75, this is not to indicate that both the electromagnetic field 69 and the millimeter wave field 75 are provided simultaneously, and either may be provided individually without the other operating, as may be desirable.

During operation of the system, the cell division rate in the present embodiment may be monitored via a cell counting device such as the FLOWCAM™ imaging system discussed herein, and the data utilized to operate, either manually or via computer control, the millimeter wave and/or Helmholtz EMF generator to optimize cellular development of the cultured organisms.

It is noted that the present bioreactor may also be used in a non-photobioreactor capacity to provide enhanced growth of non-photosynthetic organisms such as yeast cultures (for food and alcoholic production, for example), microbes or the like, and the use of the artificial and solar lighting capacities my not be required, depending upon the organism being cultured.

Once the cell count has determined to reach the optimal level for harvesting, the Helmholtz device and/or the millimeter wave device, or an exterior microwave device can be used to expose the cells (in this case, algae) to an appropriate frequency and dose of electromagnetic energy for separation of the biomass into the component lipids and polysaccharide (cellulose) fractions.

In this operation, an infusion of $CO_2$ gas is injected into either the liquid medium via the $CO_2$ infusion array (29 in FIG. 3A) or mixed with the ambient air generator system to add $CO_2$ within the flow tube 22 situated in the containment vessel 2 in order to effect a drop in the pH (acidic condition) in the liquid medium, so as to weaken the algal cell body.

A microwave, millimeter wave, or EMF source generator or the Helmholtz Coils 53, 53', are tuned to provide a pulsed energy field at a precise frequency and field strength in order to facilitate the fracturization of the cellular wall, to allow for the separation of the cellular lipids/oils from the cell detritus remaining after fracturing.

In this case, cell density may be monitored via the FLOWCAM, the appropriate microwave or other frequency for optimal cell rupture is selected, and the cell contents (lipids and polysaccharide/protein components) are separated in a settling tank.

This initial separation process may be conducted within the bioreactor or may be completed in a separate electromagnetic device set-up to function in conjunction with an exterior separation and settling tank. The device is expected to use electromagnetic field strength generated by a separate EMF generator of sufficient frequency and power output to effect the lysis of the cell walls of the algae.

Continuing with FIGS. 7-9D, to supplement the core bioreactor 1, a novel, innovative flat panel photo-type bioreactor 80 is provided, to provide enhanced natural as well as artificial sunlight exposure (for night or as otherwise required) for the growth medium, which bioreactor is exterior to the core bioreactor 1.

The flat panel bioreactor 80 was developed by the inventor to further accelerate photosynthesis by means of increasing the amount of photon exposure to the growth medium by flowing the liquid biomass through rectilinear enclosures 84, 84' exposed to natural and/or artificial sunlight. The bioreactor of the exemplary embodiment of the invention is formed of a rectilinear frame 85 having a medial divider 85' to form a barrier therebetween, dividing the frame into first 86 and second 86' cells, each cell having a length 93, a width 93', and a depth 94.

Said first cell 86 is formed to engage a front panel 82 and rear panel 83, while the second cell 86' engages and supports a separate front panel 82' and a rear panel 83', said front 82, 82' panels being opposed to and equally spaced from said rear 83, 83' panels, respectively.

The panels 82, 82', 83, 83' are preferably formed of material transparent to the wavelengths of light conducive for photosynthesis to the growth media. In the present embodiment of the invention, said sheets are formed of glass, the front panels 82, 82' spaced 101 about four inches from the rear panels 83, 83' to form first 84 and second 84' enclosures therebetween, associated with said first 86 and second 86' cells respectively.

The front 82, 82' and rear 83, 83' panels may have applied thereto a layer of inwardly 92 facing so called one-way mirror window film 93, 93' (such as manufactured by 3M of St. Paul, Minn. or the like) so as to allow the passage of light therethrough 95 for photosynthesis into each respective enclosure 84, 84', but reflect 95' any light seeking to pass out of the enclosure, in order to provide an enhanced light chamber for any photosynthetic culture (including Algae or the like) situated therein or passing therethrough. A film laminate or the like to the panels may also be used to reduce harmful UV light, while allowing the passage of optimal wavelengths of light for photosynthesis therethrough.

The rear 83, 83' panels have mounted to the frame outside of the enclosures 84, 84', projecting into said rear 83, 83' panels first and second LED grow light arrays 116, 116' and 117, 117', the exemplary embodiment utilizing SUPER-NOVA brand grow lights, 270 watt units, to provide a source of artificial grow light from the rear of the bioreactor into the enclosures where the biomass flows, providing enhanced grow light capabilities even at night, indoors, or on cloudy days.

Also mounted exterior the rear 83, 83' panels of said first 86 and second 86 cells are fluorescent tube grow lights 123, 123', 123" and 124, 124', 124", respectively, each tube being eight foot long in the present embodiment, forty watts each, to provide further artificial lighting through the rear 83, 83' panels and into their respective enclosures.

The flat panel bioreactor 80 is situated on a support frame 87 having a base 89 having first 90 and second 90' ends, and said first 90 end formed to receive and support 91 said first end 88 of said flat panel bioreactor 80, said base 89 having emanating therefrom a vertical support 96, which can be used to support (via chains, for example) the flat panel bioreactor such that the front panels 82, 82' face the sun. A hinged support beam 91 having first 97 and second 97' ends is provided, said first end 97 pivotally engaging 98 said base 89, said second end 97 engaging said panel frame 87 to support the flat panel bioreactor 80 in the proper angle 99 to various positions receive maximum sun exposure 100, which angle 99 can vary depending upon the latitude and the season.

In operation, the water or growth medium borne biomass will gravity flow (enhanced via hydrostatic head pressure in the bioreactor containment vessel 2) from the bottom of the main 4000 gallon core reactor containment vessel 2 to split 103 via T 106 or the like to flow to the bottom or first end 102, 102' of the first 84 and second 84' enclosures (glass framed four inch deep) forming the flat panel bioreactor 80 (exemplary embodiment measuring 8 feet by 8 feet) where the water borne biomass flows (or is pumped via diaphragm or bellows pump) out 110 of perforated line 109, 109', each line having three longitudinally aligned rows of perforations situated on one side of the hose, the first 111 and third 112 perforated rows may be oriented at an angle (for example about forty-five degrees) relative to the rear 83, 83' and front 82, 82' panels respectively, the second, perforated row 113 aligned with the rear and front panels, so that the water borne biomass flows along the through the width of each of said first 84 and second 84' enclosures.

In the exemplary embodiment of the present invention, it is noted that the hydrostatic head pressure of the fluid within the core reactor (bioreactor containment vessel 2) will fill the panel reactor without a pump, when the bottom level 120 of the flat panel reactor is lower than the higher fluid level 122 within the containment vessel 2 of the core reactor.

The perforated line 109, 109' in the exemplary embodiment comprises 1½ inch diameter PVC pipe with ⅜ inch diameter holes on top and both sides of pipe spaced 6" apart for six feet.

In addition, a 1" diameter diffuser hose 114 aligned with and situated adjacent to the perforated line 109 provides sterilized/filtered air (same source of air as used in air lifts 28, 40, that is, an externally located, energy efficient 2.5 HP regenerative air blower to provide filtered, UV sterilized air) to provide bubbles 115 for lift as well as for fixing PH and selectively providing CO2 for the algae or other biomass flowing through the flat panel bioreactor 80. The pressurized air bubbles provide a positive pressure within the flat bioreactor panel, which creates pressure within the enclosures to lift the water oxygenation.

The exemplary embodiment of the present invention utilizes for the diffuser hose 114 the SIEMENS brand FLEX-LINE™ fine bubble diffuser hose, providing air bubbles as well as CO2 to the system when required while enhancing flow//lift in the flat panel reactor enclosures as well as circulate the biomass between the core reactor and the present flat panel reactor without necessarily the need for an electrical pump.

A bellows or diaphragm pump 119, when used, ejects the biomass through the perforated line 109 into the reactor in the exemplary embodiment at about 60 gallons per minute from the core reactor.

The water borne biomass, upon being ejected through the perforated line 109, commingles with bubbles 115, the flows upward to the second, upper ends 104, 104' of each said enclosures 84, 84' respectively, where the water borne biomass and bubbles 115 flow out 105 of each said first 84 and second 84' enclosures via hoses 116, 116' where each of the flows are joined 107 to return returned to the upper portion 108 of the core reactor 1, where the water borne biomass and bubbles are drained into the annulus between the inside wall of the containment vessel and flow tube, for reincorporation into the core bioreactor flow and further EMF stimulation as previously discussed.

The water borne biomass, when pumped into the flat panel bioreactor with a 1 HP diaphragm pump, for example, pulses into the enclosure via the perforated line 109, 109', which, with the bubbles 115, creates turbulence 125 inside of the enclosures 84, 84' to enhance photon contact from natural or artificial light energy beamed into the enclosures. It is estimated with the present system that flow in the flat panel bioreactor can exceed 3600 gallons per hour. The flow in the enclosures is pressurized with the air/water borne biomass, which forces the biomass to flow back to the core reactor via the return hose as discussed above.

In the flat panel bioreactor, the injection via diffuser hose 114 of the purified air/co2 mixture, with the diaphragm pump, pumped in water borne biomass, provides turbulence to keep the glass clean and keep the debris in suspension, rotation in the cell air bubbles keep backside of glass screen clear. The bubbles provide an airlift action to flow by gravity the biomass from the core reactor, fill up the panel full of water, and pumps the water borne biomass with bubbles to top and out of the flat panel bioreactor, so the diffuser air in effect can "pump" the biomass laden water without the need for the diaphragm, bellows or other pump. As indicated, because the flat panel bioreactor is a sealed unit, it becomes pressurized creates enough pressure to lift the water through both panels and into the top of the reactor, fifteen foot of head to lift it. At a 65 gallons/min flow rate, the flat panel bioreactor can circulate the entire biomass of the main reactor every hour or two.

As shown, the flat panel bioreactor 80 is positioned so that the glass plates face the arc of the sun as it tracks across the sky. Such an arrangement would, naturally, be positioned so that it is directly exposed to the sun and ideally maintained via a motorized sun tracking device.

It is estimated that 100 of the bioreactors described in the present invention, arranged and operating in serial production mode, have the potential to produce some 100 or more barrels per day of algae bio-crude, in addition to 10 metric tons of a concentrated algae biomass, useful for pharmaceutical, human or animal nutrition applications.

Figure 10:
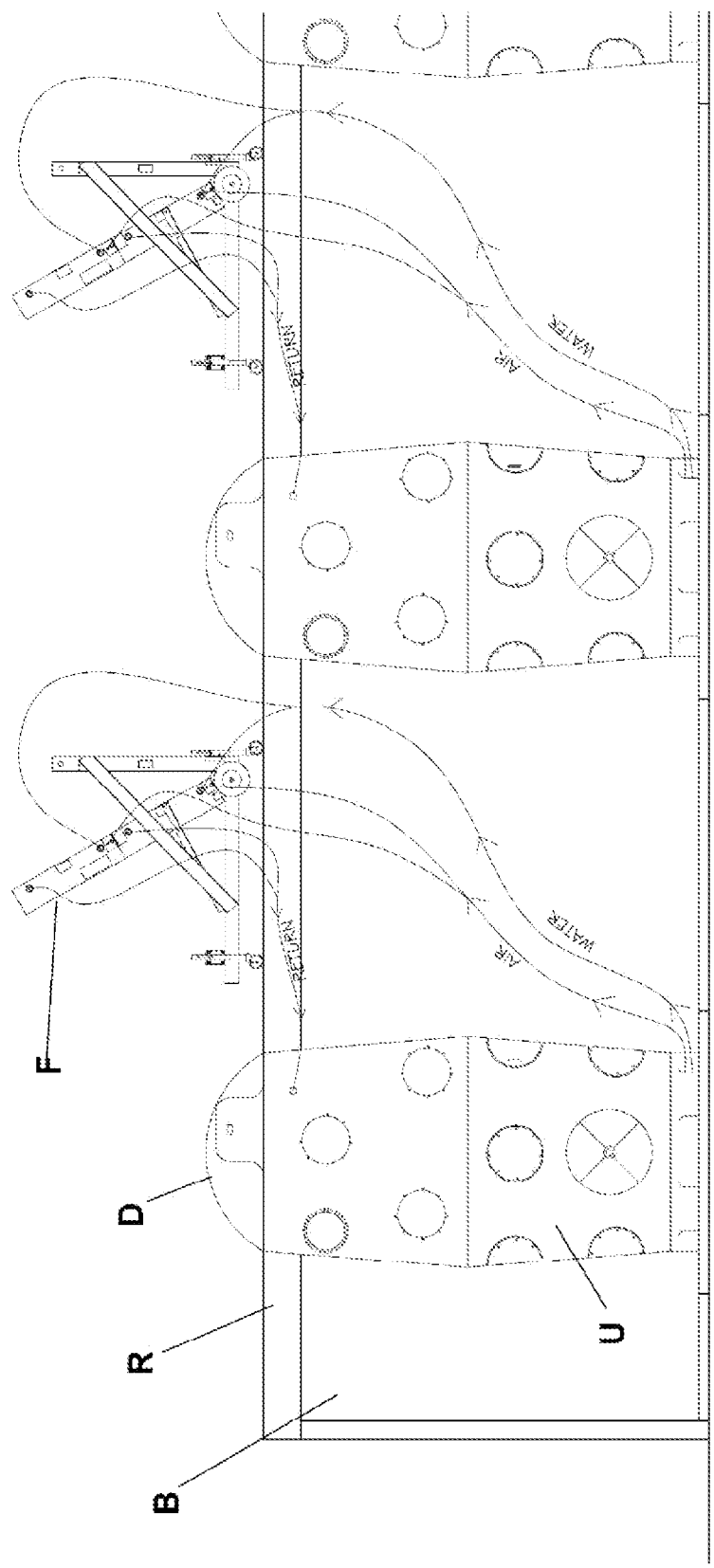
FIG. 10 is a side view of the flat panel bioreactor supporting the core bioreactor, illustrating multiple units mounted in an array in a unique facility structure (partially shown).
Figure 10A:
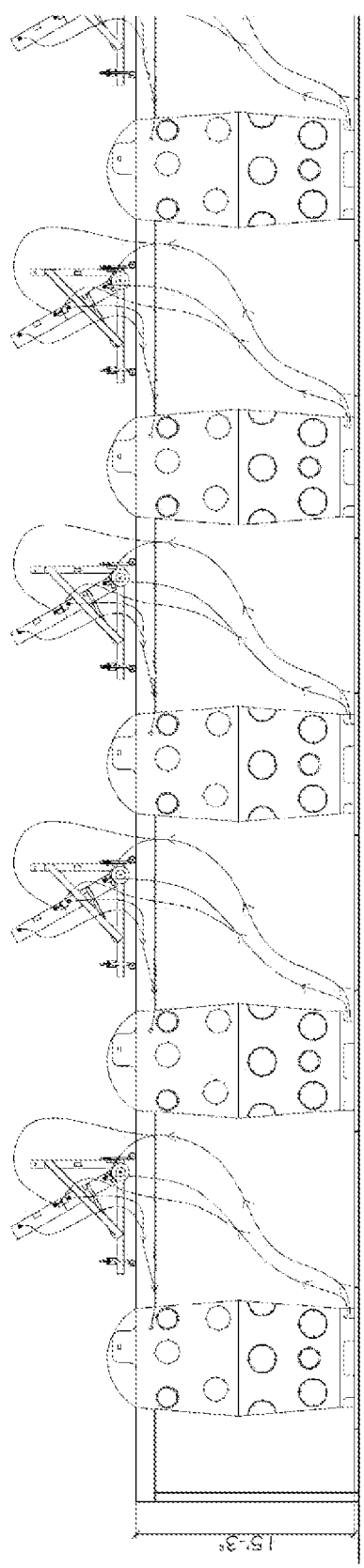
FIG. 10A is a side view of FIG. 10, illustrating more bioreactors and partial facility structure.
Figure 10C:
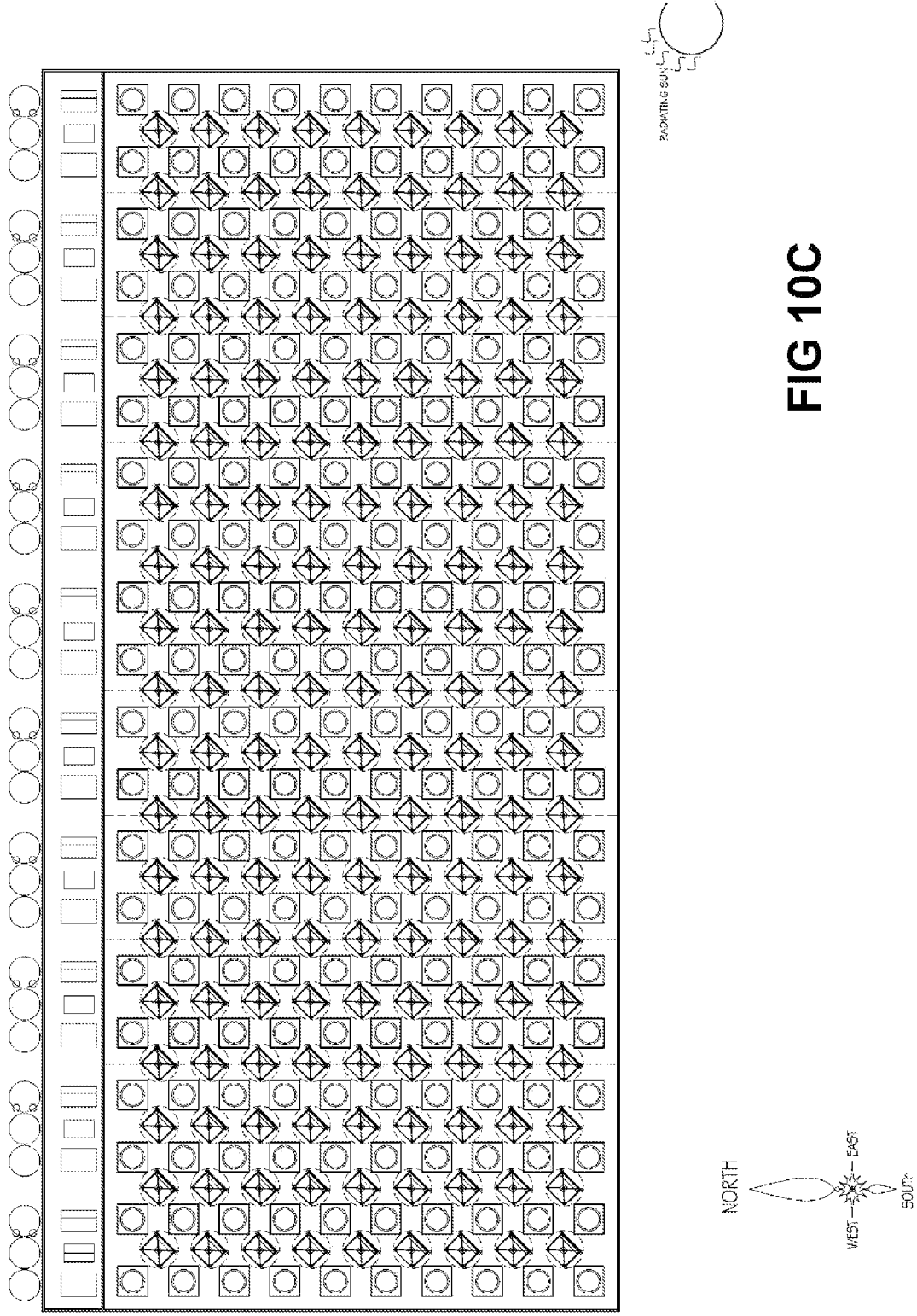
FIG. 10C is a top view of an array of bioreactors in a complete facility structure.
Figure 11:
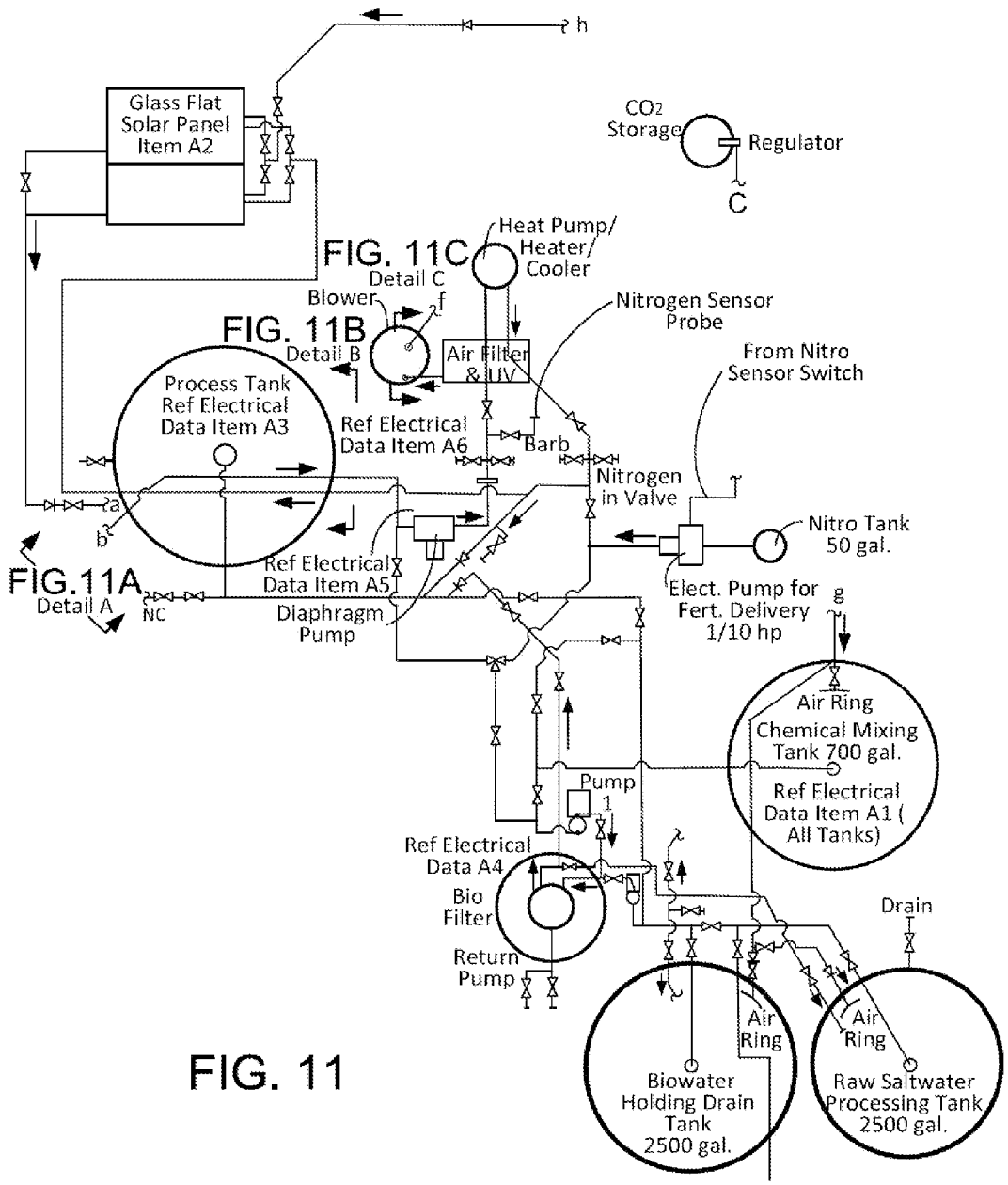
FIG. 11 is a project flow diagram of the exemplary embodiment of the present invention.

As shown in FIGS. 10-10C, a large number of 4000 or larger gallon bioreactor units U can be placed within a building B with a corresponding number of the flat panel bioreactors F on the roof R (like photovoltaic panels) for concentrating solar energy circulated below into the algae biomass bioreactor system inside of a temperature controlled building, with the domes D of the bioreactors penetrating the roof R to capture the natural sunlight. Many other applications and locations are suitable in both cold and warm weather climate.

In the bioreactor of the present invention, a recirculating air collection system in the form of a collection conduit in the upper portion of the bioreactor 1 can be used to collect air contained in the airspace (including O2 which may be generated by algae or other plant organism) above the water level and in the main dome, which air may be passed through a membrane CO2/O2 separator or the like, where the CO2 and O2 may be separated and O2 stored, utilized, or vented, while the CO2 may be stored and selectively recirculated into the bioreactor via the CO2 infusion array 29 (FIG. 3A) also be provided for collecting CO2 to prevent emissions into the atmosphere, as well as acting as a biomass processor.

Exterior systems to support the core bioreactor of the present system include a control system for the lower and upper air lifts which provides forced air thereto on demand via an air-supply line for a regenerative blower system. The system preferably includes as a feature air purification (via air filtration—four air filters in the exemplary embodiment and UV sterilization—four 60 watt ultraviolet lamps in a cabinet expose the air flow to sterilizing UV radiation in the exemplary embodiment) associated with the regenerative air blower.

Also provided exterior the core bioreactor 1 are CO2/pH monitors to monitor the CO2 and pH levels in the bioreactor and control output of CO2 via the CO2 infuser within the flow tube (or via CO2 added to the air upper or lower air lifts, depending upon the application), an automatic water heater system for maintaining optimal temperature of the growth medium/liquid in the bioreactor (discussed below), regenerative blowers, and electrical supply and switching devices. If the PH goes over 8.5 in the system when cultivating species of algae, for example, the system can be set to adjust the PH downward to 8.4 or 8.2 pH via adding CO2.

A liquid carbon dioxide storage container or other CO2 source for regulated dispersing of CO2 into bioreactor via the CO2 infuser in the flow tube 22, with a control module receiving CO2 and pH information from sensors at the bioreactor, to automatically control pH levels in the growth medium during cell growth via the CO2 infusion system, referenced above.

As the present system utilizes a controlled, sterile atmosphere including forced air (via the airlift tubes 28, 40) for circulation, it is important to maintain a positive pressure within the bioreactor vessel to prevent contamination from outside the atmosphere.

As the system is pressurized (it is estimated that the present exemplary embodiment may be pressurized up to about 10 PSI), it is important to incorporate a pressure relief mechanism into the system to avoid over pressurization.

Accordingly, two (2) pressure-relief systems in the present exemplary embodiment run from line vents in the top dome area of the bioreactor and down the side (east side in the exemplary embodiment) of the unit as primary and secondary vessel pressure controls, respectively. Also, a pressure-lock valve may be provided to open and close the vent for venting and pressurization, respectively.

It is important to note that the air-lift system discussed above is not only desirable, but provides a unique, non-destructive system to circulate the liquid/algae suspension within the bioreactor, as algae and many other micro-organisms which can be propagated within this system may stop reproducing or die when subjected to the high-stress velocities created in centrifugal type pumps.

For this reason, any pumping into or out of the system should not use centrifugal or impeller-type pumps, instead a more gentle diaphragm or bellows-type water pumps should be used.

Also not shown is a separate, exterior fiberglass growth medium preparation and holding tank (in the present embodiment of the invention comprising 2,500 gallons), which may be used to prepare the grown medium and other preparation and treatment steps involving the transfer of sterilized freshwater or seawater prior to incorporation into the growth medium.

In order to monitor the bioreactor contents during production, high-side and low side specimen monitoring and sampling unit ports are provided exterior the bioreactor containment vessel 2 of the exemplary embodiment of the present invention. Also, a valve controlled passage may be provided through the containment vessel 2 for a fluid injection (for injecting fluid into the bioreactor) or drainage system (to drain from the bioreactor), which can be selectively controlled via valves and tees.

In addition, a 4-inch-diameter algal-filtration system return line 62 (FIG. 1) and valve is provided for returning growth medium back into the bioreactor after organism filtration.

Figure 4:
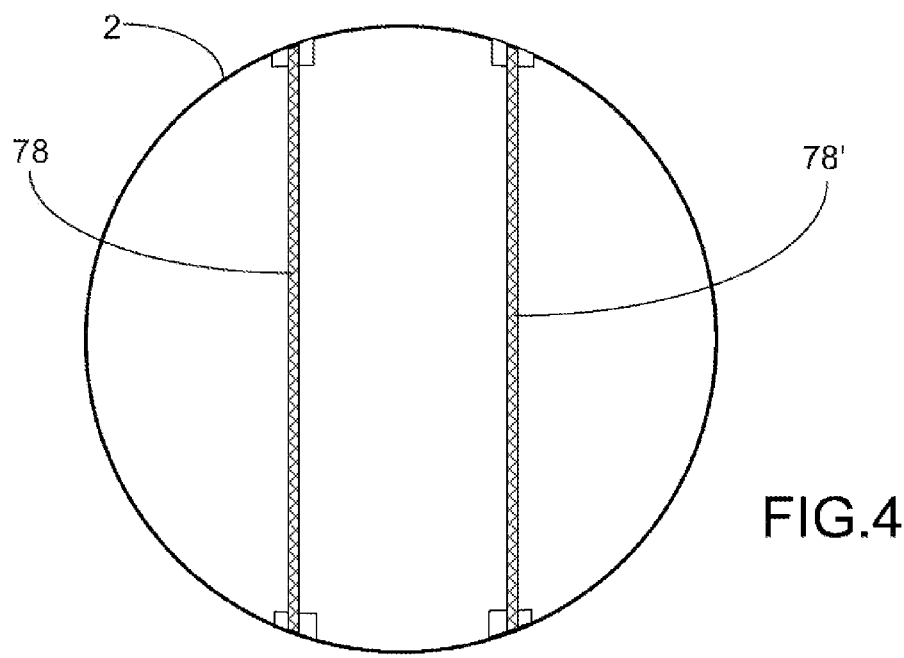

Referencing FIG. 4, heat exchangers 78, 78' or the like can be provided to form a longitudinally-situated central passage through the bioreactor vessel, for adjusting the temperature of the fluid therein while forming the central column for circulation within the bioreactor containment vessel 2.

Check valves should be used where required to prevent reverse flow and contamination, such as to prevent backflow of growth medium into the regenerative air blower, while another check valve may be provided to keep water from back flowing through the CO2 diffusers out the system.

As discussed, the cell division rate in the present embodiment can be monitored by a continuous digital cell-counting device, referenced in the exemplary embodiment as the FLOWCAM imaging system, which utilizes flow cytometry and microscopy and automatically count, image, and analyze the cells in a discrete sample or a continuous flow, providing data instantly to allow monitoring of cellular health and growth rates up to 500 million cells per ml of fluid.

A growth medium supply line, or other line from the containment vessel 2 can thus be used to provides samples to the for electronic laser particle counting, to automatically determine the cell size, as well as count the number of cells per milliliter of water, providing valuable information for monitoring and cultivating the species within the bioreactor with maximum efficiency.

For processing algae or other appropriate matter which has been harvested by the present system, the CATLIQ™ brand biomass conversion system can be used to make the wet algae biomass into bio-crude oil for further refinement into green fuels, nutrients and chemicals.

Other features not shown in the figures may include: A power-washing system built into the upper and lower sections of the bioreactor inner body for the purpose of cleaning and for chemical sterilization of the bioreactor, in which numerous high-pressure spray nozzles are provided and strategically located in each half of the bioreactor. The power-washing system may be powered by, for example, a high (for example, 5,000-PSI) pressure washer.

A 9-foot-long by 8-foot-diameter, clear acrylic cylinder may be built between the upper and lower fiberglass body section to add additional natural solar energy penetration through the 8-foot-diameter center of the bioreactor.

An "algae fence" system (for example, 8-foot-long by 8-foot-wide by 4-inch-thick panel) comprising multiple aligned tubes connected to one another at their opposing ends to provide a linear flow through each tube individually, or concurrent flow through all simultaneously, the tubes arranged to provide a radial curvature approximating that of the outer bioreactor containment vessel, can be attached to the bioreactor to pump growth medium from the bioreactor to give the organisms increased photon exposure for photosynthesis.

The exemplary embodiment of the present invention utilizes three fiberglass storage tanks for sterilizing sea water, mixing nutrient and chemical prior to and during the initial or final biomass growing process, as well as for temporary holding of the biomass that supplies the core or flat bioreactors, or while servicing the bioreactors. The same 2.5 Hp regenerative blower which supplies the air lifts in the main core bioreactor as well as the flat panel bioreactor is also used to provide in the present system air and CO2 injection and turbulence in these three referenced fiberglass storage tanks; thus, only a single 2.5 Hp regenerative blower is required to support the entire referenced system of the exemplary embodiment of the present invention.

As discussed above, a transparent dome of acrylic or the like may be provided for allowing natural solar light transmission into the top of the tank forming the bioreaction chamber. In addition, a transparent dome may also be provided at the distal, lower end of the tank also forming to enhance natural light exposure within the bioreactor containment vessel. In an alternative to the LED encased domes disclosed above, light ports may be formed in nontransparent components forming the bioreactor vessel, and/or artificial lights (such as the LED capable of producing the desired wavelength to provide photons of the proper frequency for facilitating photosynthesis) may be provided for providing a photon source to the system on a continuous basis.

A nitrogen-sensor probe should be provided with the core bioreactor to monitor and control the amount of nitrogen feed that is automatically pumped (via nitrogen source) into the bioreactor to feed organisms as required during cellular growth. A separate supply tank to feed the core bioreactor with liquid fertilizer from the nitrogen sensor triggers the supply pump that administers liquid fertilizer than shuts down the fertilizer pump. The nitrogen feeder line would go into the core reactor via a ½ inch line inserted into the discharge side of the mud pump just upstream of the Ph probe. The nitrogen probe arrangement is similar to the arrangement of the Ph monitoring probe and system.

A CATLIQ™ biomass conversion system would be acceptable to make the wet algae biomass into bio-crude oil for further refinement into green fuels, nutrients and chemicals.

Exemplary Specification:
Organism: *Nannochloropsis oculata*
Photon exposure: 52 μmol photons $m^{-2} s^{-1}$
Temperature: 21° C.
pH: 8.4 (can vary slightly)
Aeration: 14.7 VVH

ELEMENT LISTING

Description
1 core bioreactor
2 containment vessel
3 base
4,4' first, second stacked sections
5 flange
6, 6' lower, upper ends
7 medial section
8 main dome
9, 9' walls
10, 10' openings
11 domes
12 enclosure
13 light source
14 LED array
15 light energy
16,' inside, outside wall
17 sidewall
18 cover
19 air inlet
20 length
21,' ID, OD
22 bioreactor flow tube 23,' first, second open ends
24 medial portion
26,' lower flow cutouts
27 diameter
28 lower airlift tubes
29 CO2 infusion array
30,' diffusers
31 floating gate valve
32 ring body
33,' OD lower airlift tube, gate valve
34 sidewall
35 first, second ends
36,' flow apertures
37 longitudinal passage
38,' spacing, length
39 passage
40 upper airlift tube
41 interior
42 base
43,' ring or coil tube
44 CO2 supply Hose
45 membrane
46,' first second ends ring body
47 length
48,' outer, inner diameters
49 surface
50,' lower stops
51,' flow apertures
52,' upper stops
53,' helmholtz coils
54 spaced Helmholtz coils
54' bloater solution return port
55 fluid level
56 airlift bubbles
57 liquid suspension, bloater
58 flow upward
59 passes
60 flow downward
61 through lower flow cutouts 26
62 4" algae filtration return
63,' 12" observation panels
64 full fluid level
65 lift
66 space
67 flowing through
68 air lift
69 magnetic field
70 centered
71 natural sunlight from dome
72 downward flow
73 millimeter wave generator
74 power supply/control module
75 EMF
76 EMF shield
78,' heat exchangers
79 exiting
80 flat panel bioreactor
81 water level
82,' front panel
83,' rear panel
84.' enclosure
85 frame, divider
86,' cells
87, frame
88,' first, second ends
89, base
90,' first, second ends
91 hinged support beam
92, inwardly
93,' length, width
94 depth
95; reflect, passes therethrough, 96 vertical support
97, 97' ends hinged support beam
98 pivotal engagement
99 angle
100 sun exposure
101 spaced
102,' enclosure first ends
103
104,' enclosure second ends
105 out
106 T
107 joined
108 upper section
109 perforated line
110 flows out
111 first perforated row
112 third perforated row
113 second perforated row
114,' diffuser hose
115 bubbles
116,' grow lights
117,' grow lights
118,' positions
119 diaphragm pump
120 bottom level
121 lower
122 higher fluid level
123''' fluorescent tube grow light
124''' fluorescent tube grow light
125 turbulence
U core bioreactor
B building
R roof
D dome
F flat panel bioreactor Referring to FIGS. 11 and 11A-11C, a flow diagram is shown for the exemplary embodiment of the present invention, having electrical data as follows:

Item A1 (3 Tanks) 1 Each 40 Watt 120 Volt
Four foot Fluorescent Fixture @UV Rated Fluorescent Grow Light, 100 Watt Each, controlled by timer or photocell, 3000 watts@120 Volts, 2.5 Amps.
Item A2 Bio Plate Filter, 2 Each, 5 Lamp, 40 Watt. Eight foot fluorescent fixture @200 Watts each 1.7 amps.
2 GA: Ft Strip Fixture, Fitted @ Two 90 Watt LED Grow Light Module 180 Watts, 1.5 amp
Total Item A2 Load 3.2 Amps (may be controlled by Timer or Photo Cell).
Item A3 Bio Reactor, 18 Each 90 Watt LED Grow Light Controlled by Photo Cell or Timer, 1620 Watts @ 120 Volt, 13.5 Amps.
Item A4 Sand Filter, 2 Each Fractional HP Pump 9.9 Amp Ratio@4.5 Amps 120v each.
Item A5 Diaphragm Pump 1 HP @ 120 Volts, 16.0 Amp
Item A6 Blower Motor 4½ HP @240 Volts, 19.6 Amps
One each array UV Sterilizing Lamp 120 volt 0.83 Amps
Total 20.4 Amps The invention embodiments herein described are done so in detail for exemplary purposes only, and may be subject to different variations in configuration relative to design, structure, application, and operation methodology. Thus, the detailed disclosures therein should be interpreted in an illustrative, exemplary manner, and not in a limited sense.

I claim:

1. A bioreactor, comprising:
   a containment vessel having a wall having inner and outer sides forming an interior having an inner diameter, lower and upper ends, and a medial area therebetween;
   a generally vertically oriented flow tube concentrically situated in said interior of said containment vessel, said flow tube forming a longitudinal passage having a bottom, a top, and a medial area therebetween;
   said flow tube having laterally formed therethrough, in the vicinity of said medial area of said longitudinal passage, a medial flow aperture;
   a sliding gate valve comprising a buoyant, cylindrical body formed to slidingly engage said wall of said flow tube so as to selectively block flow through said medial flow aperture upon said interior of said containment vessel being filled to a predetermined fluid level.

2. The bioreactor of claim 1, wherein there is further provided an auxiliary flat panel bioreactor in fluid communication with said containment vessel, said auxiliary flat panel bioreactor having a top side and an underside comprising:
   first and second panels mounted in a spaced fashion to define an enclosure therebetween, said first panel formed of light permeable material, said enclosure having a length and first and second ends, said first panel defining said top side of said auxiliary flat panel bioreactor, said second panel defining said underside of said auxiliary flat panel bioreactor;
   a first tube having a length, said first tube formed to disperse into said enclosure flowing matter, said first tube situated in the vicinity of said first end of said enclosure;
   wherein said auxiliary flat panel bioreactor is situated exterior to said containment vessel, said enclosure is formed to receive a flow of liquid biomass suspension from said containment vessel via said first tube, and said auxiliary flat panel bioreactor is formed to facilitate the passage of said flow of liquid biomass suspension through said enclosure so as to receive light energy radiating therein.

3. The bioreactor of claim 2, wherein said auxiliary flat panel bioreactor further comprises a diffuser situated adjacent and linearly aligned with said first tube, said diffuser being formed to receive and diffuse gas therefrom so as to urge biomass and fluid in said liquid biomass suspension, provide turbulence in said enclosure to enhance exposure of biomass in said liquid biomass suspension to said light energy as it flows through said enclosure, and facilitate the flow of said liquid biomass suspension from said enclosure to said containment vessel.

4. The bioreactor of claim 3, wherein said second panel of said auxiliary flat panel bioreactor is formed of a light permeable material, and wherein there is further provided an artificial light source mounted to project light through said second panel into said enclosure, so as to radiate light energy into said enclosure.

5. The bioreactor of claim 2, wherein said first and second panels of said bioreactor comprise a layer of one-way reflective material formed to prevent light from passing out of said enclosure, said one-way reflective material formed to allow the one-way passage of light through said first and second panels into said enclosure, respectively, so as to form a reflective light chamber between said first and second panels, so as to better expose said light to any flowing matter passing therethrough.

6. The bioreactor system of claim 2, wherein there is further provided a diaphragm pump formed to provide a surging flow of liquid biomass suspension from said containment vessel to said auxiliary flat panel bioreactor, and through said first tube of said auxiliary flat panel bioreactor, so as to provide enhanced flow through said enclosure and back to said containment vessel.

7. The bioreactor of claim 1, wherein said cylindrical body of said sliding gate valve has formed therethrough a flow passage.

8. The bioreactor of claim 7, wherein said flow tube has mounted thereto a lower stop situated below said medial flow aperture, and wherein said lower stop is positioned to support said cylindrical body of said sliding gate valve such that said flow passage of said cylindrical body is aligned with said medial flow aperture of said flow tube, so as to allow the flow of matter therethrough.

9. The bioreactor of claim 8, wherein said flow tube has mounted thereto an upper stop situated above said medial flow aperture, wherein said upper stop is positioned to stop upward migration of said cylindrical body of said sliding gate valve due to buoyancy, such that said cylindrical body of said sliding gate valve blocks said medial flow aperture formed in said flow tube, to substantially prevent the passage of fluid therethrough.

10. The bioreactor of claim 1, wherein said flow tube has mounted thereto an upper stop situated above said medial flow aperture, wherein said upper stop is positioned to stop upward migration of said cylindrical body of said sliding gate valve due to buoyancy, so as to position said cylindrical body of said sliding gate valve to block said medial flow aperture formed in said flow tube, so as to substantially prevent the passage of fluid therethrough.

11. The bioreactor of claim 10, wherein there is provided a lower airlift in said flow tube below said medial area of said flow tube, said lower airlift formed to provide a pressure gradient to provide lift in said flow tube.

12. The bioreactor of claim 11, wherein there is provided an upper airlift in said flow tube above said medial area of said flow tube, said upper airlift formed to provide a pressure gradient so as to provide lift in said flow tube.

13. The bioreactor of claim 12, wherein there is further provided first and second coils concentrically mounted to said flow tube above said medial area of said flow tube, said first and second coils mounted in spaced fashion along the length of said flow tube to selectively provide a tuned electromagnetic field within and about said flow tube.

14. The bioreactor of claim 13, wherein said first and second coils comprise a Helmholtz coil, said diameter of said flow tube is about four feet, and said first and second coils are spaced about 24.5 inches apart.

15. The bioreactor of claim 12, wherein there is further provided a dome mounted to said upper end of said containment vessel, said dome being transparent to light, said dome defining a headspace above said top of said flow tube whereby matter flowing from said top of said flow tube is exposed to light from said dome.

16. The bioreactor of claim 15, wherein there is further provided a millimeter wave emitter mounted to said dome, said millimeter wave emitter formed to project millimeter waves into said headspace defined by said dome, such that flow from said top of said flow tube is exposed to said millimeter waves.

17. The bioreactor of claim 16, wherein there is further provided in said flow tube a $CO_2$ infusion array formed to selectively infuse $CO_2$ into said flow tube.

18. The bioreactor of claim 16, wherein said wall of said containment vessel has formed therethrough ports, each said port covered via a port cover formed of fluid impermeable, light transmissive material.

19. The bioreactor of claim 18, wherein said port further comprises an artificial light source mounted so as to project light into said interior of said containment vessel at each said port cover.

20. The bioreactor of claim 19, wherein said artificial light source comprises an LED array.

21. The bioreactor of claim 20, wherein said port cover comprises a dome having a convex side in said interior of said containment vessel, said dome also having a concave side defining an enclosure, wherein said LED array of said light source is mounted.

22. The bioreactor of claim 21, wherein said dome has a base having a flange, said flange mounted to said wall of said containment vessel, and wherein said base has mounted thereto a cover formed to protect said LED array from environmental conditions outside of said containment vessel.

23. The bioreactor of claim 22, wherein said cover has a vent formed therein to allow the passage of air exterior said containment vessel therethrough to cool said LED array.

24. The bioreactor of claim 12, wherein said upper and lower airlift each comprise first and second perforated hose coils, respectively.

25. The bioreactor of claim 1, wherein there is a ≥10% difference in the inner diameter of said interior of said containment vessel at said lower and upper ends of said containment vessel when compared to the inner diameter of said containment vessel at its medial area, so as to provide a flow configuration wherein the longitudinal flow of matter between said inner walls of said containment vessel and said flow tube results in an increase of turbulence therein.

26. The bioreactor of claim 25, wherein said flow configuration is formed so as to facilitate the infusion of CO2 and air into the matter.

27. The bioreactor of claim 1, wherein the inner diameter of said interior of said containment vessel at said lower and upper ends is less than the inner diameter of said containment vessel at said medial area, such that longitudinal flow of matter between said inner walls of said containment vessel and said flow tube encounter an increase in turbulence.

28. The bioreactor of claim 1, wherein said inner diameter of said interior of said containment vessel at said upper and lower ends is at least 10% less than said inner diameter of said interior of said containment area at said medial area.

29. The bioreactor of claim 1, wherein the wall defining said passage of said flow tube has a light absorbent surface, and the outer surface of said flow tube has a light reflective surface.

30. The bioreactor of claim 29, wherein said inner side of said wall forming said containment vessel has a light reflective surface.

31. The bioreactor of claim 29, wherein said light reflective surface of said inner side of said wall forming said containment vessel further comprises an application of light reflective paint having situated thereupon about ¼ pound of 12-20 mesh size, airport grade glass beads being evenly spread per square foot.

32. A bioreactor, comprising:
  a containment vessel having a wall having inner and outer sides forming an interior having an inner diameter, lower and upper ends, and a medial area therebetween;
  a generally vertically oriented flow tube concentrically situated in said interior of said containment vessel, said flow tube forming a longitudinal passage having a bottom, a top, and a medial area therebetween;
  said flow tube having laterally formed therethrough, in the vicinity of said medial area of said longitudinal passage, a medial flow aperture;
  a sliding gate valve comprising a buoyant, cylindrical body formed to slidingly engage said wall of said flow tube so as to selectively block flow through said medial flow aperture upon said interior of said containment vessel being filled to a predetermined fluid level;
  an auxiliary flat panel bioreactor in fluid communication with said containment vessel, said auxiliary flat panel bioreactor having a top side and an underside comprising:
    first and second panels mounted in a spaced fashion to define an enclosure therebetween, said first panel formed of light permeable material, said enclosure having a length and first and second ends, said first panel defining said top side of said auxiliary flat panel bioreactor, said second panel defining said underside of said auxiliary flat panel bioreactor;
    wherein said auxiliary flat panel bioreactor is situated exterior to said containment vessel, said enclosure is formed to receive a flow of liquid biomass suspension from said containment vessel, and said auxiliary flat panel bioreactor formed to facilitate the passage of said flow of liquid biomass suspension through said enclosure so as to receive light energy radiating therein.

33. The bioreactor of claim 32, wherein said auxiliary flat panel bioreactor further comprises a diffuser, said diffuser being formed to receive and diffuse gas therefrom so as to urge biomass and fluid in said liquid biomass suspension through said enclosure, while providing turbulence in said enclosure to enhance exposure of biomass in said liquid biomass suspension to said light energy as it flows through said enclosure.

34. The bioreactor of claim 33, wherein said second panel of said auxiliary flat panel bioreactor is formed of a light permeable material, and wherein there is further provided an artificial light source mounted to project light through said second panel into said enclosure, so as to radiate light energy into said enclosure.

35. The bioreactor of claim 34, wherein said first and second panels of said bioreactor comprise a layer of one-way reflective material formed to prevent light from passing out of said enclosure, said one-way reflective material formed to allow the one-way passage of light through said first and second panels into said enclosure, respectively, so as to form a reflective light chamber between said first and second panels, so as to better expose said light to any flowing matter passing therethrough.

36. The bioreactor system of claim 35, wherein there is further provided a diaphragm pump formed to provide a surging flow of liquid biomass suspension from said containment vessel to said auxiliary flat panel bioreactor, and through said first tube of said auxiliary flat panel bioreactor, so as to provide enhanced flow through said enclosure and back to said containment vessel.

* * * * *